(12) United States Patent
Dreyer

(10) Patent No.: US 10,839,959 B2
(45) Date of Patent: Nov. 17, 2020

(54) SYSTEM AND METHOD AND GRAPHICAL INTERFACE FOR PERFORMING PREDICTIVE ANALYSIS AND PRESCRIPTIVE REMEDIATION OF PATIENT FLOW AND CARE DELIVERY BOTTLENECKS WITHIN EMERGENCY DEPARTMENTS AND HOSPITAL SYSTEMS

(71) Applicant: Jeffrey Randall Dreyer, Columbus, OH (US)

(72) Inventor: Jeffrey Randall Dreyer, Columbus, OH (US)

( * ) Notice: Subject to any disclaimer, the term of this patent is extended or adjusted under 35 U.S.C. 154(b) by 432 days.

(21) Appl. No.: 15/581,228

(22) Filed: Apr. 28, 2017

(65) Prior Publication Data

US 2018/0314802 A1    Nov. 1, 2018

(51) Int. Cl.
*G16H 40/20* (2018.01)
*G16H 40/63* (2018.01)

(52) U.S. Cl.
CPC ............. *G16H 40/20* (2018.01); *G16H 40/63* (2018.01)

(58) Field of Classification Search
CPC ................................ G16H 40/20; G16H 40/63
See application file for complete search history.

(56) References Cited

U.S. PATENT DOCUMENTS

| | | | |
|---|---|---|---|
| 10,128,000 B1 * | 11/2018 | Zhou | G16H 40/20 |
| 2003/0050794 A1 | 3/2003 | Keck | |
| 2007/0129983 A1 * | 6/2007 | Scherpbier | G06Q 50/22 705/2 |
| 2007/0239484 A1 * | 10/2007 | Arond | G06Q 10/0637 705/2 |
| 2011/0054946 A1 * | 3/2011 | Coulter | G06Q 10/06 705/3 |
| 2014/0108033 A1 * | 4/2014 | Akbay | G06Q 50/22 705/2 |
| 2016/0048642 A1 * | 2/2016 | Brooks | G06Q 50/22 705/2 |
| 2017/0185721 A1 * | 6/2017 | Schuck | G06F 3/0481 |

* cited by examiner

*Primary Examiner* — Fonya M Long
*Assistant Examiner* — Anthony Michael Balaj
(74) *Attorney, Agent, or Firm* — Standley Law Group LLP; James L. Kwak

(57) ABSTRACT

A system and method for tracking emergency room patients, resources and queues and for providing a unified graphical interface structure for facilitating process flow improvements and resource management. The system has a graphical user interface adapted to display in a first screen, the graphical interface having a triage region, bed status region, and patient arrival and acuity surge regions. The specific structure and layout of the graphical user interface aids the hospital staff in quickly and efficiently providing a graphical and unified view of hospital process bottlenecks and resource availability and opportunities. The system analyzes resources and predicts needed actions and alerts appropriate staff and notifies of prescribed actions.

73 Claims, 26 Drawing Sheets

Figure 8

| Alerts | ESCALATION LEVEL | | | |
|---|---|---|---|---|
| | Hospital Surge Level 0 | Hospital Surge Level 1 | Hospital Surge Level 2 | Hospital Surge Level 3 |
| Hospital Demand - capacity after 2pm (using lowest number in the current hospital demand box) | <19 | >20 | >30 | >40 |
| | AND | AND | AND | AND |
| ED Escalation level | Any | ED Escalation Level 3 | ED Escalation Level 2 | ED Escalation Level 1 |
| | OR | OR | OR | OR |
| | Don't Alert IF: | Don't Alert IF: | Don't Alert IF: | Don't Alert IF: |
| | | If any other level 2 or 3 Hospital Surge Alert has fired in the 16 hours | If any other level 3 hospital Surge Alert has fired in the last 16 hours | None |
| All Clinical Nurse Managers and unit coordinators | | Hospital Surge Level 1: Report to your unit, assess for potential discharges and notify Patient placement, assist in discharges and pulling admits to your floor | Hospital Surge Level 2: Report to your unit, assess for potential discharges and notify Patient placement, assist in discharges and pulling admits to your floor, call in additional 2 staff members if needed. | Hospital Surge Level 3: Report to your unit, assess for potential discharges and notify Patient placement, assist in discharges and pulling admits to your floor. Call in additional 3 staff members if needed |
| PACU manager and Unit coordinator | | Hospital Surge Level 1: Hold PACU patient in PACU until notified | Hospital Surge Level 2: Hold PACU patient in PACU until notified call in additional staff to hold patients overnight | Hospital Surge Level 3: Hold PACU patient in PACU until notified call in additional staff to hold patients overnight |
| Surgery Manager | | None | Assess Operating schedule, coordinate with Surgeons need to cancel elective surgeries needing admission | Assess Operating schedule, coordinate with Surgeons need to cancel elective surgeries needing admission |
| EVS Manager | | Hospital Surge Level 1, call in additional staff to clean beds, communicate with Patient placement to deploy staff | Hospital Surge Level 2 call in additional staff to clean beds as needed, communicate with Patient placement to deploy staff | Hospital Surge Level 3, call in additional staff to clean beds as needed, communicate with Patient placement to deploy staff |
| Radiology Manager | | Hospital Surge Level 1, call in additional staff if CT queue >3, Notify Radiologist on call of need for rapid reading or ED CTs | Hospital Surge Level 1, call in additional staff if CT queue >3, Notify Radiologist on call of need for rapid reading or ED CTs | Hospital Surge Level 1, call in additional staff if CT queue >3, Notify Radiologist on call of need for rapid reading or ED CTs |
| Transportation manager | | Hospital Surge Level 1, call in additional staff to transport if needed | Hospital Surge Level 1, call in additional staff to transport if needed | Hospital Surge Level 1, call in additional staff to transport if needed |
| House Supervisor | | Hospital Surge Level 1, Assist Patient placement in prioritizing placement of ED Admissions | Hospital Surge Level 2, Assist Patient placement in prioritizing placement of ED Admissions | Hospital Surge Level 3, Assist Patient placement in placing PACU and ED patients |
| Patient Placement Manager | | Hospital Surge Level 1: coordinate with staff to turn over beds ASAP, prioritize Placement of ED Patients | Hospital Surge Level 2, coordinate with staff to turn over beds ASAP, prioritize Placement of ED Patients | Hospital Surge Level 3, Assist Patient placement in placing PACU and ED patients |
| ED Medical Director | | Call in Additional ED physician | Call in Additional Physician Assistant or Nurse Practitioner | |
| CMO | | | Hospital Surge Level 1 | Hospital Surge Level 2 | Assist surgery manager in contacting attending surgeons to cancel elective surgeries |
| Transfer Center | | Hospital Surge Level 1, consult with CMO any transfers from outside facilities | Hospital Surge Level 2, consult with CMO any transfers from outside facilities | Hospital Surge Level 3, Divert transfers from outside facilities |
| CNO | | Hospital Surge Level 1, open overflow beds, call in additional Staff | Hospital Surge Level 2, open overflow beds, call in additional Staff | Hospital Surge Level 3, open overflow beds, call in additional Staff |
| COO or administrator on call | | Hospital Surge Level 1, open command center and coordinate operational efforts | Hospital Surge Level 2, open command center and coordinate operational efforts | Hospital Surge Level 3, open command center and coordinate operational efforts |
| CEO | | Hospital Surge Level 1 | Hospital Surge Level 2 | Hospital Surge Level 3 |

Figure 26

SYSTEM AND METHOD AND GRAPHICAL INTERFACE FOR PERFORMING PREDICTIVE ANALYSIS AND PRESCRIPTIVE REMEDIATION OF PATIENT FLOW AND CARE DELIVERY BOTTLENECKS WITHIN EMERGENCY DEPARTMENTS AND HOSPITAL SYSTEMS

BACKGROUND OF THE INVENTIVE FIELD

The present invention is directed to field of managing resources in hospitals. More specifically, the present invention relates to a system and method for facilitating the identification of bottlenecks and problem areas in emergency room and patient care processes by tracking and providing a unique graphical user interface structure that presents a unique combination of features and data in an interactive, unified, graphical manner. The present invention also provides a uniquely structured interface for presenting hospital demand and capacity versus daily planned occupancy and for providing escalating alerts to predetermined hospital staff based on combinations of information. The present invention tracks patient arrival demand and capacity, arrival volume and hospital demand capacity by time of day to prescribe actions by staff and management.

Currently, live streaming multisource data that analyzes, identifies, monitors and alerts users of system bottlenecks does not exist. There is currently no system that identifies, in a live environment, variations in testing and treatment flow. Furthermore, no system presently exists that measures queue depth of each process step, and alert's management, in an escalating fashion, when queue depth, time in queue or a combination of the two is above specified levels. Additionally, there is no system that presents the combination of features and data in a uniquely structured interface as the present invention that allows hospital staff and management to quickly assess the current status of emergency queues when compared to historical patterns and in combination with critical resources to make quick determinations about staffing, resource allocation, and other decisions to correct problem areas. As a result, hospitals and emergency departments (ED) are inefficient, causing patients to wait for care. Each year, 136.3 million patients visit U.S. emergency departments.

In over 25% of our nation's 5,000 emergency departments, the average wait time to see a physician is over 30 minutes and over 45 minutes for academic hospitals. Waiting for care increases time to treatment for many critical diseases. Waiting for care decreases the quality of care and increases morbidity, mortality and expense. The cause is multifactorial and includes inefficient utilization of hospital and emergency department bed resources, due to poor processes in testing, treating and dispositioning patients and management of these resources.

Hospital beds are at a shortage with most hospitals operating at over 90% capacity. Inefficient hospital bed turnover leads to bottlenecks in transporting ED admitted patients and other admitted patients to these beds. in most hospitals, between 60 and 80% of the patients in hospital beds come through the ED. Inefficient ED flow causes patients to IL BS which impacts the hospital's reputation, revenue reimbursement, and effects patient care quality. Managing the flow of hospitalized patients discharge and subsequent bed turnover a management challenge as most admissions and discharges occur between 11 am and 9 pm. Before the present invention, there was no system that live streams multisource data and analyzes, identifies, monitors and alerts hospital staff of system bottlenecks. The hospital bed is a highly utilized resource that requires coordinated management of outgoing and incoming patients. A comprehensive system that analyzes all inputs, predicts outcomes, and provides a solution does not exist. Furthermore, prior to the present invention, there is no solution to the problem of providing an interface for providing the necessary information in a unified, interactive, and graphical matter for:

facilitating the identification of bottlenecks in the patient care process, facilitating visualization of historic and current emergency dept, patient queue and arrival patterns and arrival and acuity surge patterns to predict future outcomes, facilitating the prioritization and mobilization of resources (e.g., staff and beds) to improve the flow of patient care;

facilitating the visualization of emergency room bed opportunities.

real time monitoring of daily planned and anticipated hospital admissions, potential and confirmed hospital discharges and the orchestration of the bedding of patients from the ED, OR, cardiology catheterization lab, and other areas in relationship to available resources, staffing, and emergency department arrival pattern.

For example, the system and method of the present invention tracks and provides the following data in a unified and graphical user interface structure:

i. patient queues (queue depth and time in queue) at various stages of patient care (e.g., lobby patient queue, patients awaiting ED beds, patients awaiting specialized psychiatric (e.g., J Pod) beds, emergency department patients' admission status number and duration);

ii. process queues—times at various stages of patient care (e.g., lab x-rays, tests, pharmacy);

iii. resource queues—awaiting resource that is currently in use (e.g., CT scanner that is in use, ED admitted patients awaiting empty hospital bed, patient awaiting blood draw from busy nurse);

iv. emergency room patients who left without being seen (LWBS) (which represents a failure of patient flow);

v. current longest lobby wait time;

vi. hourly arrival surge—compared to historic arrival pattern by hour;

vii. daily arrival surge—compared to historic arrival patterns by day of week and season;

viii. EVAC (Emergency Vehicle Assistance and Communications) arrived in last hour;

ix. patient acuity surge;

x. bed census (i.e., how many beds are occupied by patients)—by bed groupings or pods;

xi. number of dirty beds in each group—and duration of time in that "dirty" status;

xii. number of clean beds in each group—and the duration of time in that "clean" status;

xiii. emergency department bed opportunities (graphically displayed in combination with bed census, no. of dirty and clean beds by group), including:

a. admitted patients with assigned hospital beds—and the duration of time they have been in that status; (which is another bed opportunity);

b. medically cleared patients (cleared to go to psychiatric area of the ED or to another facility) (bed opportunity)—and the duration of time they have been in that status;

c. pending discharge patients "Discharge Requested"—and the duration of time they have been in that status. (in other words, duration of time is the length of time the patients are in their ED beds from the time they have entered their respective statuses, e.g., once a patient has been given a status of medically cleared, the system tracks the duration of time they remain in their ED bed from the time they enter that status until they are transferred to the psychiatric pod (J Pod) or to another facility).

xiv. The system and method also assists in managing incoming admissions and monitoring patient discharge flow. The system of the present invention is adapted to track and monitor queue depth and duration of various admissions factors and automatically alerts the relevant hospital staff of the delays in an escalating fashion. The present invention realizes and accounts for delays in admissions processes that ultimately lead to delays in freeing emergency department beds to care for waiting patients. The software displays, in real time, the status of planned and anticipated admissions from ED, OR, and other areas and the census, staffing and capacity of each hospital floor and unit. The software also monitors hospital discharges and bottlenecks to discharge flow and provides status for each hospital floor and unit.

The software utilizes a unique structure for alerting hospital staff that is based on inpatient beds, status of those beds, and capacity.

SUMMARY OF THE GENERAL INVENTIVE CONCEPT

The present invention seeks to provide a solution to the problems in traditional systems. The system receives process and resource data as it is occurring in the hospital. The data is live streaming in the format used by hospitals which is Health Language 7 (HL7). The system receives the data by way of a virtual private network (VPN). For example, the system receives data from each process and testing step. HL7 data is preferably coded with a patient identification number which is unique to that patient and that visit. The data is parsed into tables and the software analyzes the data, allowing for the identification of patient care bottlenecks and resource utilization issues. After identification, the system alerts the users of the issues so that corrective action can be taken. The alerts are sent in multiple ways: e.g., by staff-worn communication devices with verbal or text message, by text message, computer screen alert and/or email messages.

The system receives data from the hospital's electronic medical record (EMR) system and bed tracking system through a secure, virtual private network (VPN). The hospital personnel do not need to input data directly into the software system. For example, in the preferred embodiment, the system uses the information that the staff inputs info theft EMR and bed scheduling software. The messages are sent as HL7 messages, HL7 is Health Language 7 which is a messaging system that caries specific patient care information. HL7 contains a unique patient identification number. The HL7 messages do not contain private health information (non-PHI); therefore, the messages are HIPPA compliant (Health Insurance Portability and Accountability Act). The hospital sends the HL7 messages via the VPN to the system servers. The HL7 messages are parsed into multiple tables in the database, where calculations of queue depth and size of process steps, resources and personnel are processed, evaluated, and packaged as specifically structured graphical interfaces for presentment to the users.

The present invention has a set of uniquely structured graphical user interfaces comprised of multiple display screens to visualize the bottlenecks, current and historic patient arrival and acuity patterns, patients who have left without being seen (LWBS), and bed resource status and opportunities. These specifically structure interfaces allowing users and management to quickly prioritize and mobilize resources to improve patient flow, therefore improving quality of care and patient safety.

The present invention facilitates the management of resources by providing an integrated dashboard view that allows users to easily visualize the conditions of the emergency room in combination with the status of the beds in the emergency room, to quickly assess the situation, and to assist in managing ED resources.

The system also assists management in predicting patient hourly volume and degree of illness surges (and in combination with historic patterns), to allow for allocation of staff and other resources. The software measures duration of care steps by providers allowing for necessary improvement.

The present invention also identifies the multiple, variable bottlenecks in patient care and resource utilization, by analyzing combinations and patterns of queues, specifically based on time in queue and queue depth, as well as time of day and day of week of occurrence.

For example, the invention analyzes the below factors and, based on the factors, alerts management of bottlenecks or anticipated bottlenecks to allow for management to plan and assist in improving patient flow.

| FACTORS ANALYZED | Additional explanation |
| --- | --- |
| Emergency Department (ED) Lobby patient current count | Alerts to ED staff if count over 8 patients |
| ED Lobby patient wait time current | Alerts ED staff if over 45 minutes |
| ED patients left without being seen (LWBS) total count | Alerts ED management each time |
| ED Patient Laboratory Order, Collection and Result | Alerts ED staff responsible for collection if collection time over 30 minutes. Alerts lab staff if test not resulted within specified time based on test. |
| ED Patient Xray Test Order, Exam Start, and Result | Alerts Radiology Technologist if test not began within specifications, Alerts Radiology staff is test not resulted within specifications |
| ED Patient Pharmacy Orders placed, medication received by ED and Administration times | Alerts Pharmacy Staff is medication not received in the ED within specified time. Alerts nurse if not administered within specified time |
| ED Patients admitted without RTM-count, duration and ED bed numbers | Alerts ED unit clerk to notify admitting physician if beyond time specifications |

-continued

| FACTORS ANALYZED | Additional explanation |
|---|---|
| ED Patients Admitted with RTM-count, duration and ED bed numbers | Alerts patient placement if count or duration above time specifications |
| ED Patients Admitted with bed assigned-count, duration and ED bed numbers | Alerts ED nurse and nurse accepting patient that admission assigned. Re-alerts at 30 minutes |
| Surgical patients with RTM number and duration | Alerts Patient Placement Department if cehsus is over 85% and if more than a predetermined number of surgical cases are pending |
| Surgical patient admitted with Bed assigned number and duration | Alerts nurses in recovery room and on floor accepting patient so patient can be transferred. Re-alerts after 30 minutes if patient not transferred. |
| Cath Lab patients with RTM number and duration | Alerts patient placement |
| Cath Lab patients with bed assigned number and duration | Alerts Cath lab and floor nurse of assigned bed. So report can be called and patient can be transferred to floor. |
| Radiology admission patients with RTM number and duration | Alerts patient placement if Radiology room is over 85% occupied and more than a predetermined number of cases are pending. |
| Radiology admission patients with bed assigned | Alerts radiology nurse and floor nurse of assigned bed so report can be called and patient transferred to floor. |
| Anticipated ED Admissions today count Current ED Admissions today count Anticipated Surgery Admissions today count Current Cath lab admissions count Anticipated Cath lab admissions count Current Radiology Admissions count Anticipated Radiology admissions count Discharges anticipated count and floor Discharges completed count and floor | Software manages and displays current status of beds in order to manage flow of patients into and out of hospital. This display of the data allows management to anticipate bed needs early in the day. The software displays the current count of each floors pending and confirmed discharges and pending admissions. Each hospital floor or unit is staffed and equipped to care for patients of different degrees of illness and illness types. Current tracking of these resources by the software alerts staff to potential and current bottlenecks. |
| Services needed on each pending discharge, | Monitors and alerts of delays and services. Alerting the services if the bed on the floor or uniti is needed on that specific unit. |

The present invention collects and analyzes patient arrival patterns to the emergency department and uses historic arrival patterns to assist in management and predicts future outcomes. For example, the present invention uses the above factors and predicts the financial loss based on anticipated emergency room (ED) volumes and emergency department patients who have left without being seen (LWBS).

The present invention also analyzes operating room schedules and admission and discharge queues and patterns, assisting in planning of inpatient bed resources. For example, every day, each hospital nursing unit inputs the discharges for that day, anticipated and definite. The surgical schedule notes potential and definite admissions and which type of nursing floor the patient will need to go. The ED has an anticipated daily admission volume and types of beds needed. The present invention performs a demand capacity model for the above and will alert the user or management of possible bottlenecks and of which patients. The surgical schedule can then be reordered to assist in patient flow from surgery to recovery to hospital bed.

The present invention also alerts users of flow problems with depth of queue or time in queue, in an escalating fashion, beginning with front-line users and escalating in a stepwise fashion to users in middle and upper management.

The software analyzes combinations of queue depth and duration, analyzes the combination of patient flow and care delivery constraint points, alerts specific users and staff, and prescribes actions to be taken by users. For example, if the ED awaiting bed queue depth and/or duration is long and the admission queue for all admissions is larger than predicted discharges, the administration is alerted to open more overflow beds and call in additional staff. If the hospital is currently below average staffing levels, the administrators would be notified, so that appropriate actions can be taken. In another example, if the queue for a specific test is long, and the predicted resources are not available and/or the number of patients awaiting an ED bed is large, the tests management personnel would be alerted of the issue and would be advised to increase resources to the specific test.

For example, in one embodiment of the system, the system is comprised of a graphical user interface adapted to display in a first screen; a processing system, the processing system programmed with instructions for executing on the processing system for: displaying in the first screen a first region comprised of a first indicator representing the number of patients waiting in the emergency department lobby; storing the number of patients waiting for admission into the hospital; storing the number patients predicted to be discharged; and sending a first alert to a predetermined staff member if the first indicator representing the number of patients waiting in the emergency department lobby is larger than a predetermined number and if the number of patients awaiting for admissions into the hospital is larger than the number of patients predicted to be discharged.

In this embodiment, the processing system is programmed with instructions for executing on the processing system for: storing the number of patients waiting in the emergency department for a medical test; storing the number of available resources for conducting the medical test; and sending a first alert to a predetermined staff member if the first indicator representing the number of patients waiting in the emergency department lobby is larger than a predetermined number and if the number of available resources for conducting the medical test is not sufficient to handle the number of patients waiting for the medical test.

Additionally, in another embodiment, the processing system is programmed with instructions for executing on the processing system for: displaying in the first screen, a bed status region; displaying in the bed status region a listing of a plurality of areas of an emergency department, bed census data for each of the plurality of areas, a listing of clean beds for each of the of the plurality of areas and a duration of time each of the clean beds have been in a clean bed status, a listing of dirty beds for each of the of the plurality of areas and a duration of time each of the dirty beds have been in a dirty bed status.

In one embodiment of the invention, the invention is comprised of a system and method for tracking and facilitating the identification of bottlenecks and problem areas in hospital emergency departments, comprising the steps of: displaying in a first screen of a graphical user interface a first region comprised of a first indicator representing the number of patients waiting in the emergency department lobby; displaying in the first screen, a bed status region; displaying in the bed status region a listing of a plurality of areas of an emergency department, bed census data for each of the plurality of areas, a listing of clean beds for each of the of the plurality of areas and a duration of time each of the clean beds have been in a clean bed status, a listing of dirty beds for each of the of the plurality of areas and a duration of time each of the dirty beds have been in a dirty bed status.

The foregoing and other features and advantages of the present invention will be apparent from the following more detailed description of the particular embodiments, as illustrated in the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 8 illustrates a screen shot of the bed status region of one embodiment of the dashboard of the present invention showing resource utilization of the emergency department beds.

FIG. 26 illustrates a table illustrating example alerts generated by the system of the present invention when taking into consideration the ED and hospital admissions dashboards.

DETAILED DESCRIPTION OF EXEMPLARY EMBODIMENT(S)

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

The present invention uses time stamp data to analyze and identify arrival patterns, processes, and patient acuity variations causing bottlenecks and inefficient use of bed resources, testing resources, staff resources, and pharmacy resources. The processes involve multiple components. These components are the hospital, the emergency department, the operating room and post-anesthesia care unit, the cardiac catheterization laboratory, and the radiologic procedure room, transfers to the hospital from other hospitals and direct admissions to the hospital.

Figure 1:
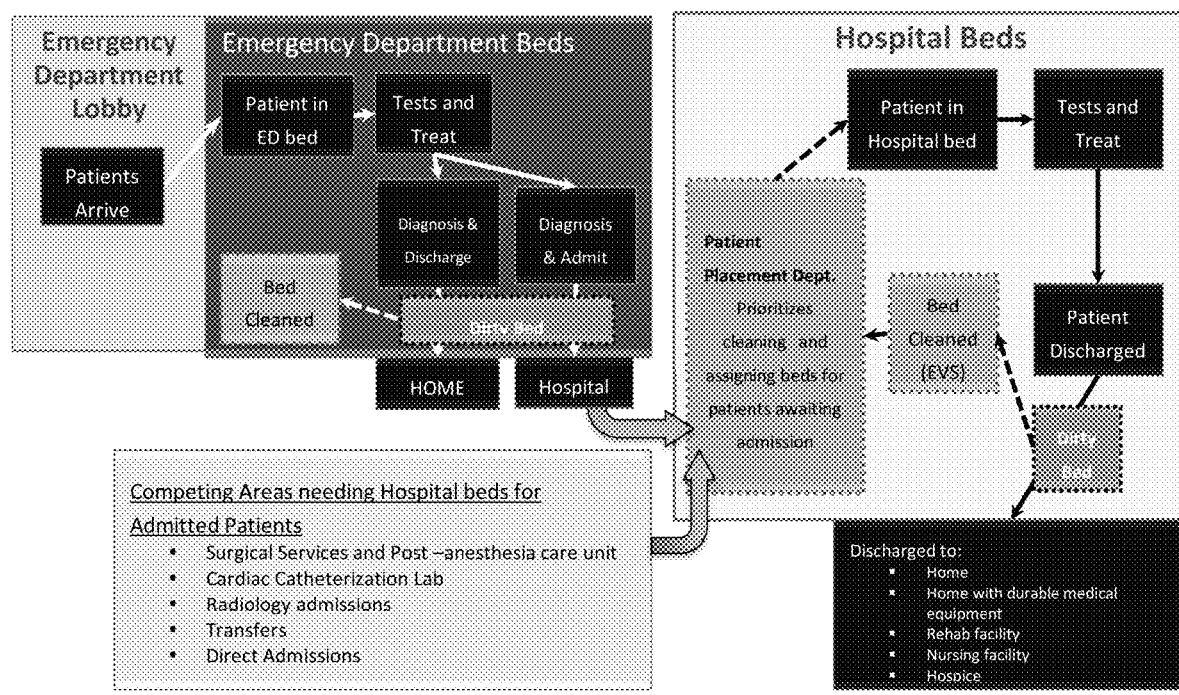
FIG. 1 illustrates one embodiment of an overview of patient care and flow. The software measures, monitors, displays and alerts the interdependencies in all the hospital departments.
Figure 2:
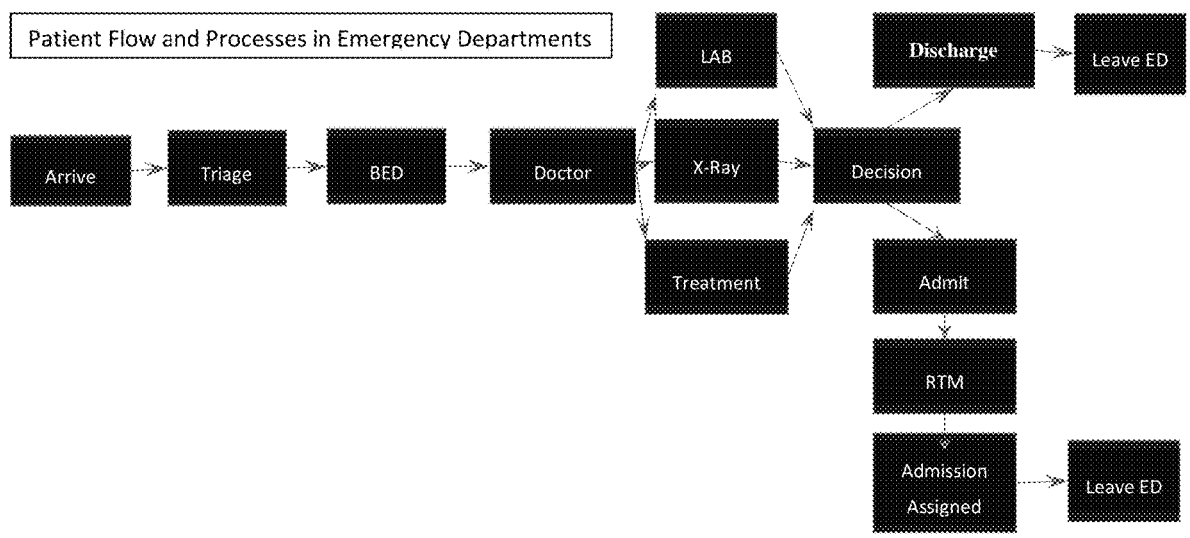
FIG. 2 illustrates the patient process flow of one embodiment of an emergency department.
Figure 3:
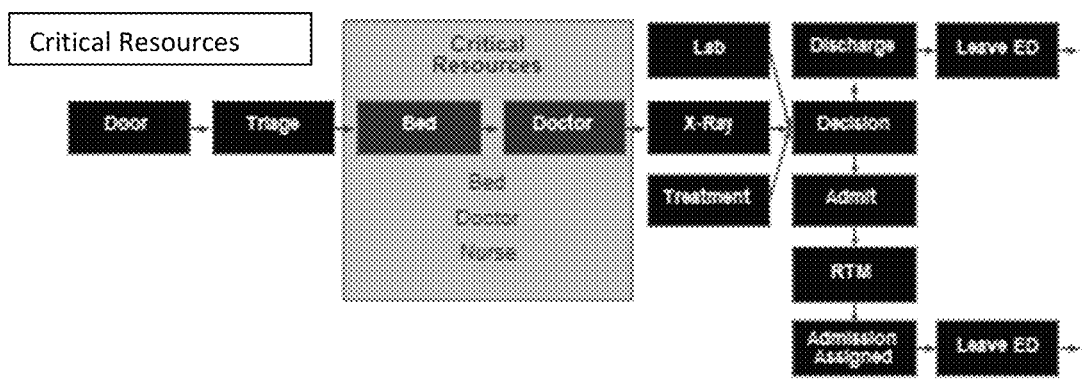
FIG. 3 illustrates one embodiment of a diagram depicting critical resources in an emergency department including a clean, unoccupied bed.
Figure 4:
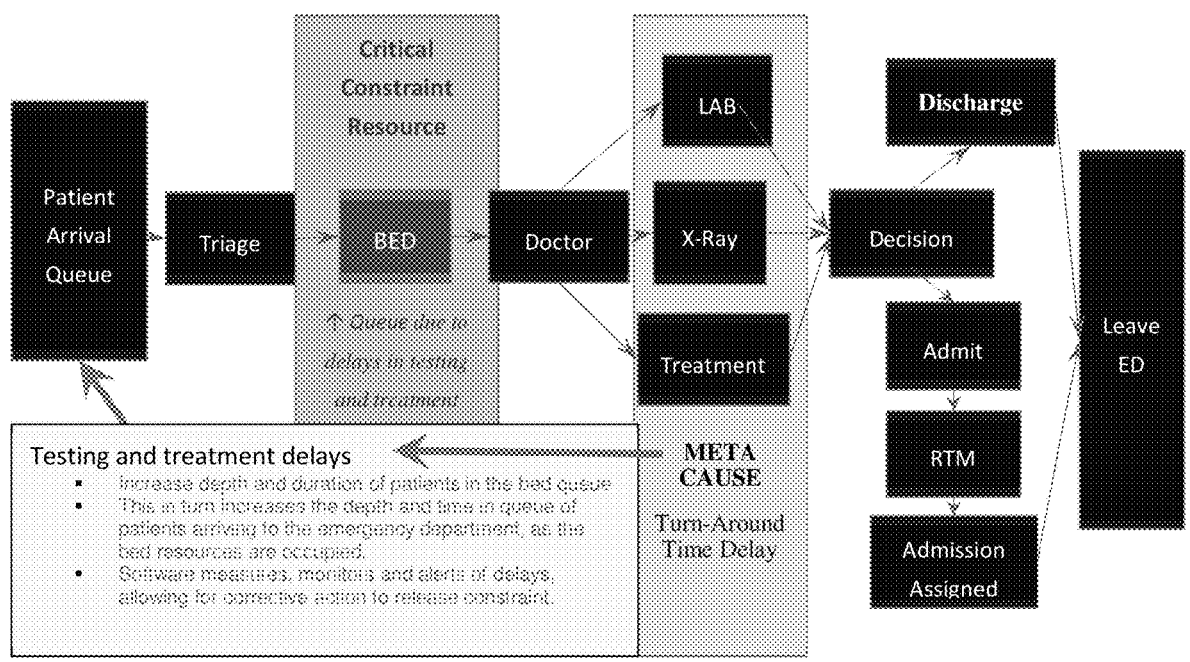
FIG. 4 illustrates one embodiment of the relationship between testing and treatment and their effect on bed availability.

FIG. 1 illustrates one embodiment of an overview of patient care and flow. The present invention measures, monitors, displays and alerts the interdependencies in all the hospital departments. FIG. 2 illustrates the patient process flow of one embodiment of an emergency department. The critical resources in the emergency department and hospital are the bed, nurse, and doctor unit. The bed is the only one of these resources with a fixed capacity. Physician and nurse work capacity fluctuate with need and assistance from others. The critical constraining resource is the ED beds and hospital beds. FIG. 3 illustrates one embodiment of a diagram depicting critical resources in an emergency department. Availability of hospital and emergency department beds are directly correlated to prolonged and variable testing and treatment times. When there are delays in the testing and treatment process, the beds are occupied longer than specifications, and patients arriving cannot be placed in beds to receive care. FIG. 4 illustrates one embodiment of the relationship between testing and treatment and their effect on bed availability.

The invention measures critical processes at the hospital using timestamps and measures each process step's queue depth and duration. If any portion falls outside of specifications or predetermined limits, the present invention alerts users so that corrective actions can be taken. The alerts are preferably sent to users in an escalating fashion with the first-level, directly-responsible staff members notified first. If the problem is not resolved, their immediate supervisor is notified. If still not resolved, the supervisor's supervisor is contacted. If queue depth is above specifications or predetermined limits, alerts are sent to supervisors to assist in resource reallocation. A "meta cause" is one of the largest, most visible or obvious issues given as the reason the hospital process is not functioning according to plan or standards. In order to relieve or resolve a meta cause, the root cause should be mitigated first.

Figure 5:
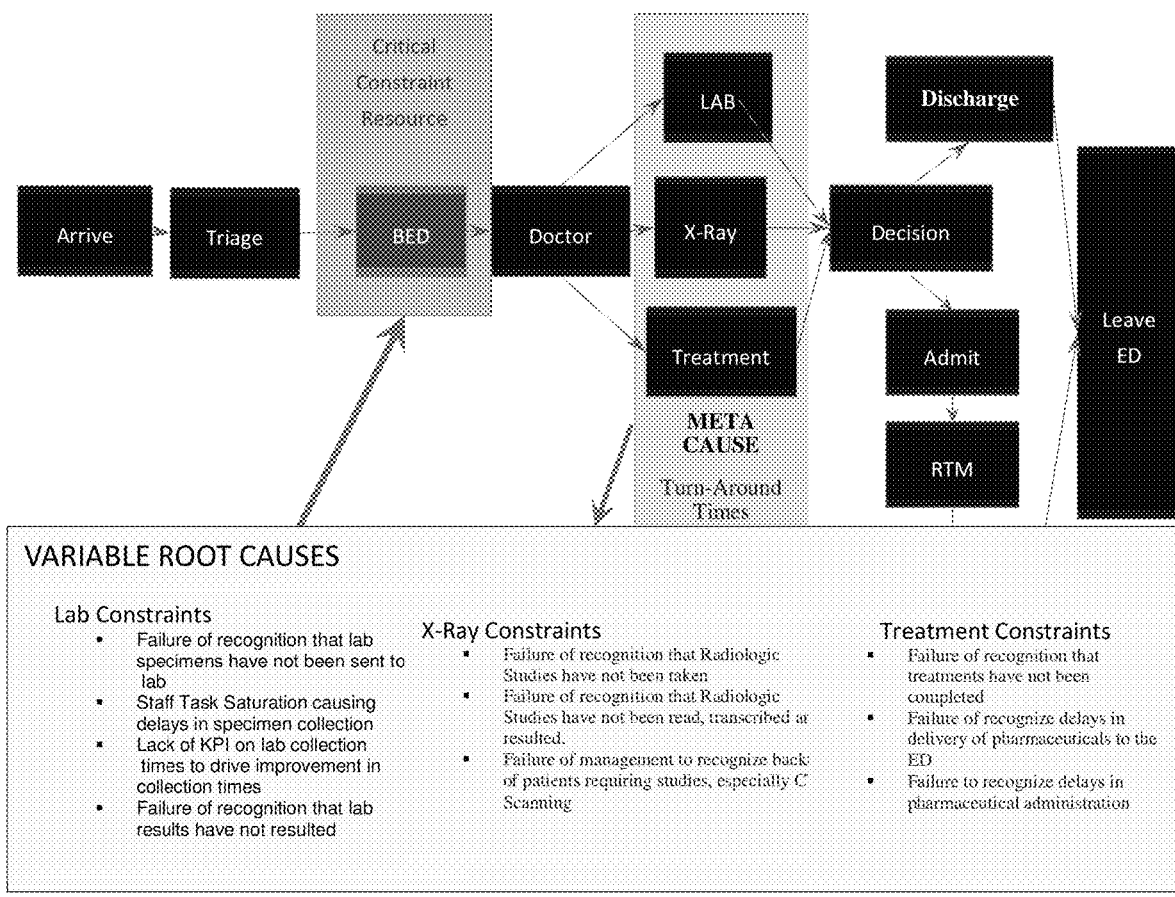
FIG. 5 illustrates the relationship between the bed (the critical constraint resource) and the root causes of the constraint are demonstrated.

FIG. 5 illustrates the relationship between the bed (the critical constraint resource) and the root cause of the constraint. For example, when the testing queue length or duration is too long, it causes patients in the ED beds to remain longer in the bed causing delays and preventing arriving ED patients from being placed in a bed.

Figure 6:
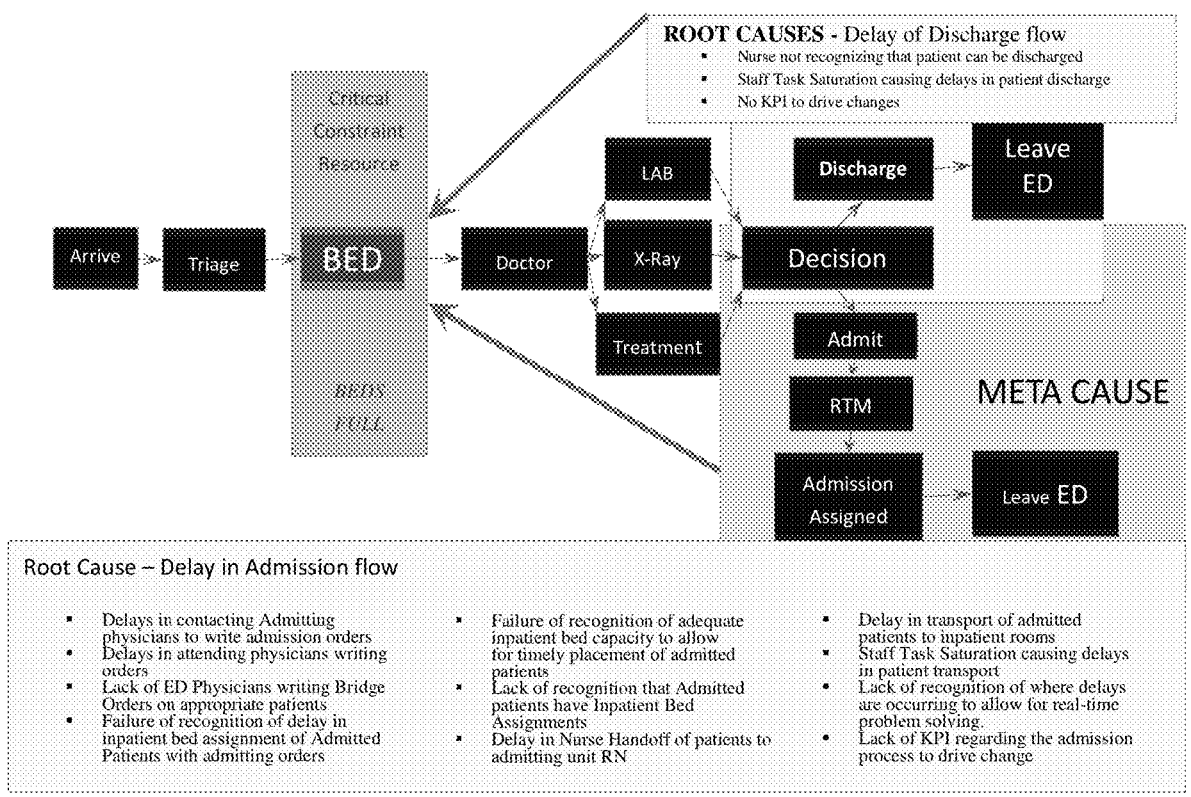
FIG. 6 illustrates admissions process steps and constraint factors that may cause delay in admission processes and bed resource availability.

Other causes of bed resource unavailability are process delays after all tests are completed. FIG. 6 illustrates admissions process steps and constraint factors that may cause delay in admission processes and bed resource availability. The physician reviews patient and test information, and decides to discharge or admit the patient. Discharge delays are recognized by the present invention and the system issues escalating alerts to users. The admission process involves multiple steps and users are alerted in escalating fashion of delays in the process. Once the bed is empty and needs cleaned, escalating alerts are sent to users alerting staff. After cleaning, the bed status is updated to the dashboard so that the next patient can be placed in this critical resource. The system alerts staff of underutilized critical bed resources (the constraint).

In many hospitals, there are multiple sources for hospital admissions. These sources often compete for the same bed resources, which further cause prolonged ED bed occupancy queue depth and duration. Admission flow is also hindered by multiple causes that the software will measure, monitor and report. These include:

| Process step measured by invention | Dependent constraints | Measure and Display | Software alerts |
| --- | --- | --- | --- |
| Time from last Test Resulted to ED physician decision to admit patient | Delays in contacting Admitting Physician to accept patient, delays in return phone call | Time in queue for each patient | Of delay in contacting admitting physician or return phone call |
| Bed request time to Ready to move time (RTM) | Constraint of having available inpatient physician causing delays in writing inpatient orders RTM | Time in queue for each patient and depth of queue | User of prolonged times and long queues |
| RTM to Inpatient bed assigned | Inpatient bed Constraint of having available unoccupied, clean inpatient bed | Time in queue for each patient and depth of queue. | User of prolonged times and long queue |
| | Admission Daily Load, types and numbers of beds needed | Anticipated admission load for ED, Surgery, cardiac catheterization lab, radiology, transfers, and direct admissions | Of bed or patient demand is greater or less than bed or resource capacity |
| | Daily inpatient Discharges anticipated | Measures and monitors inpatient bed discharges and time of discharge. | Of prolonged times and largequeue count |
| | Inpatients patients being discharged-Availability of dependent resources needed for discharge: Nursing home acceptance, Durable medical equipment, Home therapy and transport home or to another facility | Assists in identifying causes of discharge delays | Alerts specifc personell of needs for discharge and delays in discharges. |
| Inpatient bed assigned to patient leaves the ED | Constraint of having inpatient nurse and ED nurse handoff of care | Time in queue for each patient and depth of queue | User of prolonged times and large queue counts |
| Inpatient bed assigned to patient leaves the ED | Constraint of having transport availability to transport patient to inpatient bed | Time in queue for each patient and depth of queue | User of prolonged times and long queue |

The interaction of the Inpatient Bed Resource Constraints is correlated to ED bed resource constraints leading to increased queue length and time in queue for patient arriving to the ED.

Regarding ED bed constraints, the present invention analyzes, monitors and alerts to multiple opportunities for improved bed utilization. The system monitors the status of every bed in the ED e.g., is the bed clean, dirty or in use (occupied) and the length of time the bed is in this status.

The ED is a difficult environment to manage, and when patient flow diminishes the etiology is difficult to quickly identify so that the issues can be fixed. Is the issue causing poor flow due to:

1. Patient arrivals—are there more or less arriving patients than what is expected and staffed?
2. Patient acuity—Has the department had high acuity patients which demand many resources?
3. Are Admitted Patients having difficulty being admitted? If so, is the problem with the attending physicians or with bed availability?
4. Are Behavioral Health (BH) patients (psychiatric patients) having difficulty flowing into the BH Pod (J Pod) and ultimately into the hospital's BH unit?
5. Is there a delay in testing? If so, at what point, in the lab or in the collection of specimens?

Figure 7:
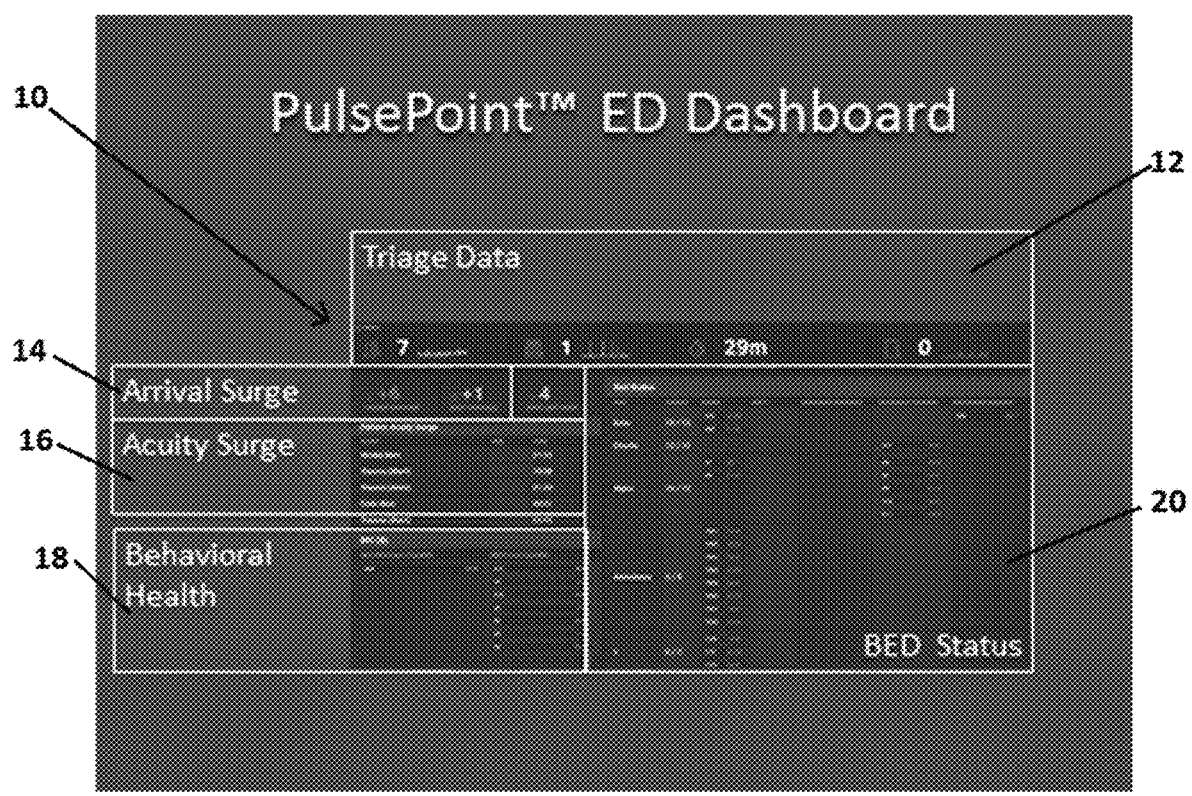
FIG. 7 illustrates a screen shot of one embodiment of the graphical user interface or dashboard of the present invention.
Figure 8:
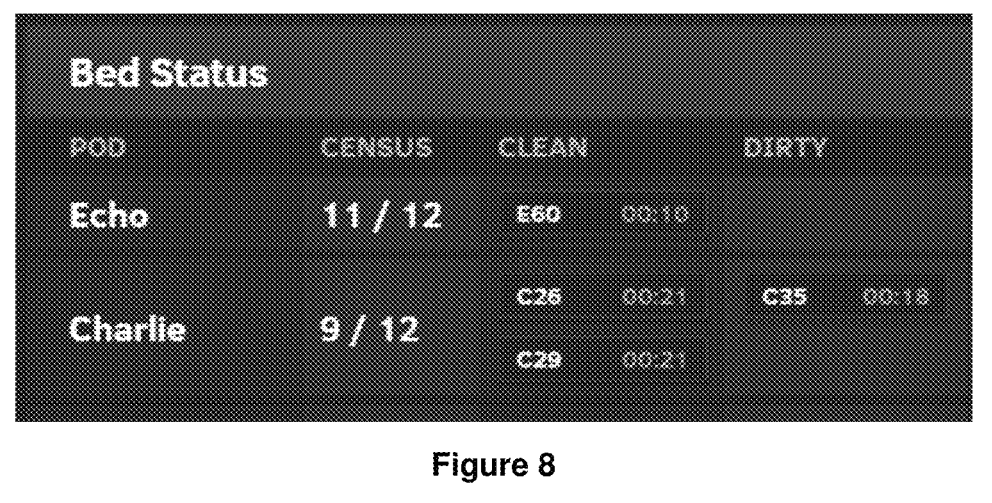

FIG. 7 illustrates a screen shot of one embodiment of the graphical user interface 10 or dashboard of the present invention. The dashboard is broken up into multiple regions: the triage region 12, the arrival surge region 14, the acuity surge region 16, the bed status region 20, and the behavioral health region 18. Each one will be described below in detail. FIG. 8 illustrates a screen shot of the bed status region of one embodiment of the dashboard of the present invention showing resource utilization of the emergency department beds. The census is the number of patients currently in the pod (or section of the emergency department), e.g., in the embodiment of FIG. 8, in pod Echo, there are 11 beds occupied by patients out of 12 beds total in the pod. A dirty bed is an unoccupied bed that needs cleaned. A clean bed is an unoccupied bed that is clean and ready for a patient. The time shown next to the dirty and clean beds is the time that the bed has been in that status in hours and minutes (hh:mm).

Figure 9:
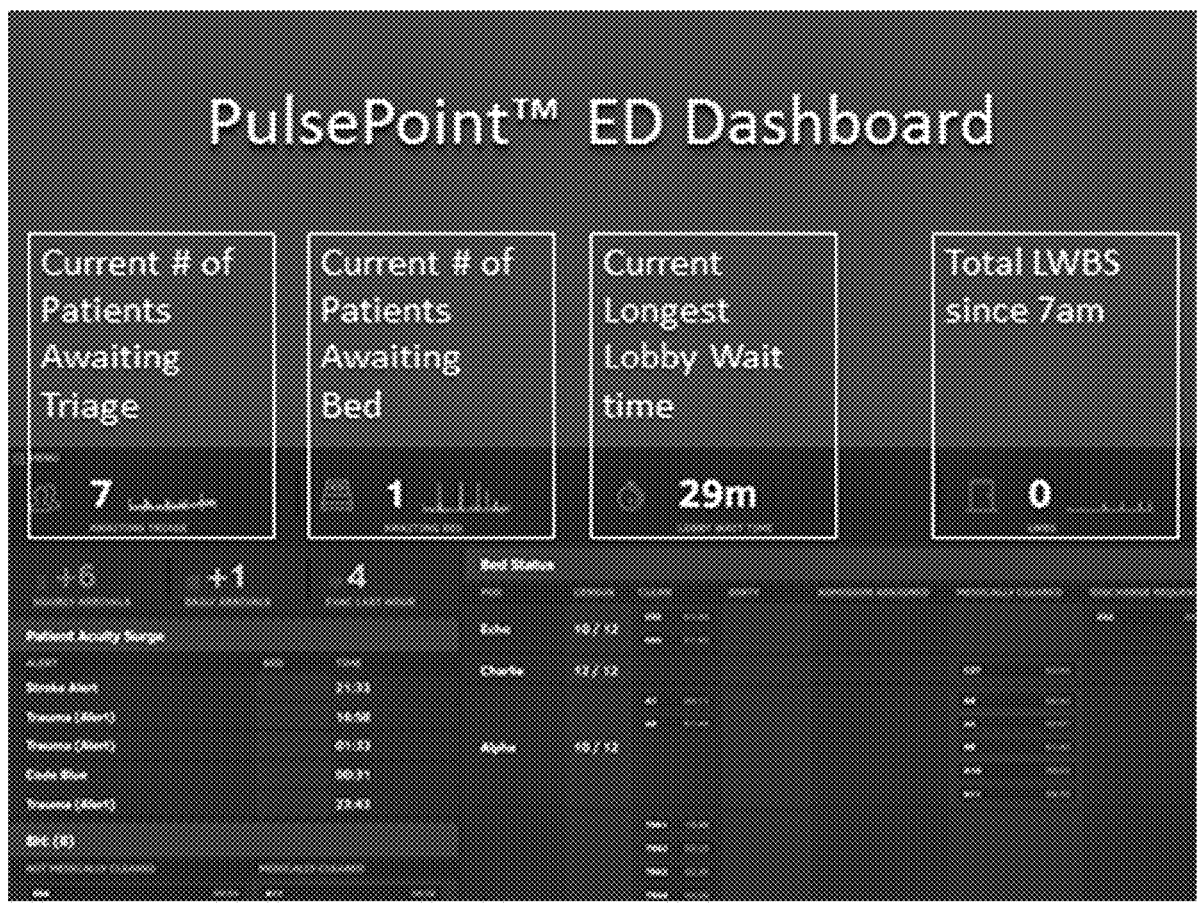
FIG. 9 illustrates the top row (triage portion) of the dashboard that shows the number of patients that have arrived and are awaiting triage, the current number that are awaiting a ED bed and the current longest lobby wait time.

FIG. 9 illustrates the top row (triage portion) of the dashboard that shows the number of patients that have arrived and are awaiting triage, the current number that are awaiting a bed and the current longest lobby wait time. In the present invention, the longest lobby waiting time is determined by looking at all patients who are currently in the ED, which is defined as patients that have arrived but have not yet left. Of these patients, the patients who have not been placed in a bed are considered the lobby patients. The patient with the longest time from arrival to being placed in a bed is the patient with the longest lobby wait time. The length of time this patient has been waiting in the lobby is shown in the region labeled "longest wait time." In this embodiment, the LWBS count is the number of patients that day, since 7 am, that have "Left Without Being Seen." A high LWBS number indicates a failure of the system that flows patients into the emergency department that requires immediate attention. The current invention sends escalating alerts to management at set levels of LWBS so that high LWBS can be averted. The invention displays all the bottlenecks for patient flow so that remedial action can be taken.

In this embodiment, escalating alerts are sent to users and management based on the duration and depth of the values. It is preferred that the alerts be generated and sent based off individual hospital characteristics. For example, one hospital may be set up with the following procedure having three alert escalation levels (1, 2, and 3).

Level 1 Escalation:
1. If more than 8 patients have arrived to the ED, but not placed in a bed; or
2. The longest lobby wait time is over 45 minutes; or
3. One patient has left before being seen (LWBS).
This alert would be sent to the nurse in charge of the ED at that time, and the clinical coordinator on duty.

Level 2 Escalation:
1. If more than 15 patients have arrived, but not placed in a bed; or
2. The longest lobby wait time is over 90 minutes; or
3. Four patients have left before being seen (LWBS).
This alert will be sent to ED nurse manager, patient placement, and hospital nursing supervisor and ED physician medical director.

Figure 10:
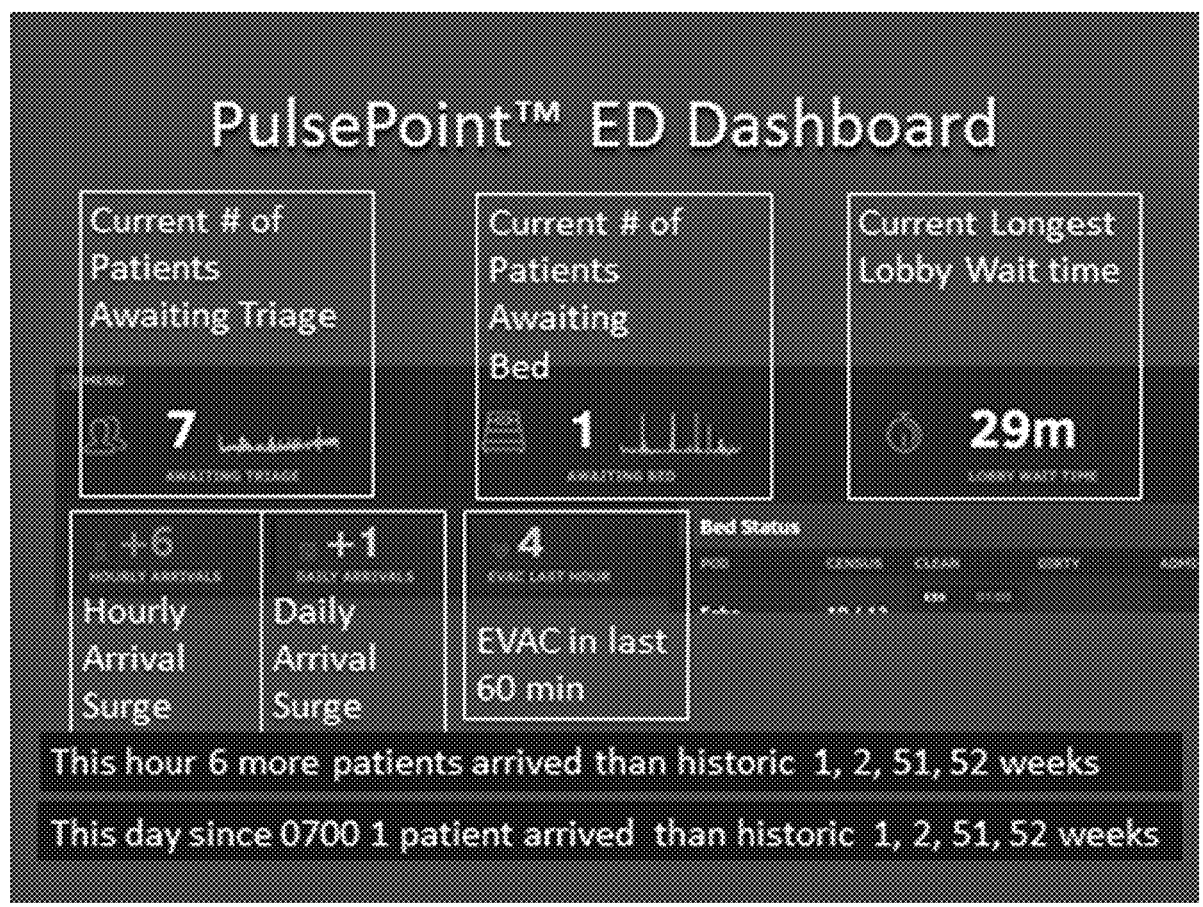
FIG. 10 illustrates a close-up view of the second row of the dashboard illustrating the patient arrival surge display region.

Level 3 Escalation:
1. If more than 20 patients have arrived, but not placed in a bed; or
2. The longest lobby wait time is over 120 minutes; or
3. Ten patients have left before being seen (LWBS).
This alert will be sent to the ED nurse manager and the Chief Nursing Officer and to the staff alerted of Level 2 escalation:

FIG. 10 illustrates a close-up view of the second row of the dashboard illustrating the patient arrival surge display region. There are hourly and daily surge values which compare to historic patient arrival patterns from the previous 1, 2, 51 and 52 weeks. As indicated on the FIG. 10, the +6 hourly arrival surge indicates that in the current hour, 6 more patients arrived than historic 1, 2, 51, and 52 week periods. Also, the +1 indicates that on the current day (since 7:00 am), 1 more patient arrived than historic 1, 2, 51 and 52 week periods.

For example, the below tables illustrate an example calculation using Feb. 9, 2017 as "today". Note that, theoretically if the current time is 3 pm on Feb. 9, 2017, the ED had 13 patients arrive between 2 p and 3 p, which is two patients below average.

| | | HOURLY ARRIVALS ABOVE OR BELOW AVERAGE | | | | | | |
|---|---|---|---|---|---|---|---|---|
| | | Year | | | | | | |
| | | 2016 | 2016 | 2017 | 2017 | | 2017 | |
| | | | | Week # | | | | |
| | | 6 | 7 | 5 | 6 | | 7 | |
| | | | | Weekday | | | | |
| | | Thurs | 4 | 4 | Thurs | Average of previous weeks | "Today" | Hourly Arrivals above or below average |
| | DATE | Feb. 4, 2016 | Feb. 11, 2016 | Jan. 26, 2017 | Feb. 2, 2017 | | Feb. 9, 2017 | |
| Hour of Day | 7 a | 8 | 12 | 8 | 4 | 8 | 7 | −1 |
| | 8 a | 12 | 6 | 12 | 14 | 11 | 11 | 0 |
| | 9 a | 18 | 16 | 14 | 15 | 16 | 13 | −3 |

HOURLY ARRIVALS ABOVE OR BELOW AVERAGE

| | Year | | | | | | |
|---|---|---|---|---|---|---|---|
| | 2016 | 2016 | 2017 | 2017 | | 2017 | |
| | Week # | | | | | | |
| | 6 | 7 | 5 | 6 | | 7 | |
| | Weekday | | | | | | |
| | Thurs | 4 | 4 | Thurs | Average of previous weeks | "Today" | Hourly Arrivals above or below average |
| DATE | Feb. 4, 2016 | Feb. 11, 2016 | Jan. 26, 2017 | Feb. 2, 2017 | | Feb. 9, 2017 | |
| 10 a | 12 | 12 | 16 | 16 | 14 | 12 | −2 |
| 11 a | 16 | 16 | 18 | 12 | 16 | 16 | 1 |
| Noon | 15 | 13 | 13 | 11 | 13 | 16 | 3 |
| 1 p | 13 | 11 | 12 | 12 | 12 | 15 | 3 |
| 2 p | 14 | 18 | 15 | 12 | 15 | 13 | −2 |
| 3 p | 14 | 11 | 16 | 15 | 14 | 17 | 3 |
| 4 p | 23 | 11 | 18 | 17 | 17 | 14 | −3 |
| 5 p | 16 | 17 | 16 | 15 | 16 | 14 | −2 |
| 6 p | 14 | 10 | 12 | 13 | 12 | 12 | 0 |
| 7 p | 14 | 14 | 12 | 13 | 13 | 12 | −1 |
| 8 p | 11 | 10 | 9 | 11 | 10 | 11 | 1 |
| 9 p | 9 | 11 | 13 | 11 | 11 | 8 | −3 |
| 10 p | 7 | 5 | 9 | 10 | 8 | 7 | −1 |
| 11 p | 10 | 7 | 6 | 5 | 7 | 8 | 1 |

The system answers the questions: Are daily arrivals above or below average? At each hour of the day, is the number of patients that the ED is seeing total, that day, at that hour above or below what is expected based on historical data? Theoretically, in this example, if today is Feb. 19, 2017 at 3 pm, the ED has had 108 patients arrive which is one less than the average.

DAILY ARRIVALS ABOVE OR BELOW AVERAGE

| Year | 2016 | 2016 | 2017 | 2017 | | 2017 | |
|---|---|---|---|---|---|---|---|
| Week # | 6 | 7 | 5 | 6 | | 7 | |
| Weekday | Thurs | 4 | 4 | Thurs | | "Today" | Daily Arrivals |
| Hour of Day | Feb. 4, 2016 | Feb. 11, 2016 | Jan. 26, 2017 | Feb. 2, 2017 | Average | Feb. 9, 2017 | Above or below average day |
| 7 a | 8 | 12 | 8 | 4 | 8 | 7 | −1 |
| 8 a | 20 | 18 | 20 | 18 | 19 | 18 | −1 |
| 9 a | 38 | 34 | 34 | 33 | 35 | 31 | −4 |
| 10 a | 50 | 46 | 50 | 49 | 49 | 43 | −6 |
| 11 a | 66 | 62 | 68 | 61 | 64 | 59 | −5 |
| Noon | 81 | 75 | 81 | 72 | 77 | 75 | −2 |
| 1 p | 94 | 86 | 93 | 84 | 89 | 90 | 1 |
| 2 p | 108 | 104 | 108 | 96 | 104 | 103 | −1 |
| 3 p | 122 | 115 | 124 | 111 | 118 | 120 | 2 |
| 4 p | 145 | 126 | 142 | 128 | 135 | 134 | −1 |
| 5 p | 161 | 143 | 158 | 143 | 151 | 148 | −3 |
| 6 p | 175 | 153 | 170 | 156 | 164 | 160 | −4 |
| 7 p | 189 | 167 | 182 | 169 | 177 | 172 | −5 |
| 8 p | 200 | 177 | 191 | 180 | 187 | 183 | −4 |
| 9 p | 209 | 188 | 204 | 191 | 198 | 191 | −7 |
| 10 p | 216 | 193 | 213 | 201 | 206 | 198 | −8 |
| 11 p | 226 | 200 | 219 | 206 | 213 | 206 | −7 |

This information is valuable because, by looking at the patient surge values, hospital staff can denote if the problems with patient flow are related to an above average number of arriving patients. This is important because the staffing levels of EDs varies by the hour of day, and the ED staffing is determined by evaluating the average arrivals and average ED census. That said, the ED is staffed to care for the average number of patients and census, based on historic levels. If the ED is showing a backup of patients in the lobby or a high number of LWBS, and the hourly and daily arrivals are normal, that signals the management to look at other reasons for the backup. If the ED is backed up and the daily arrivals are much greater than expected, management can add additional staff to cover the excess.

Figure 11:
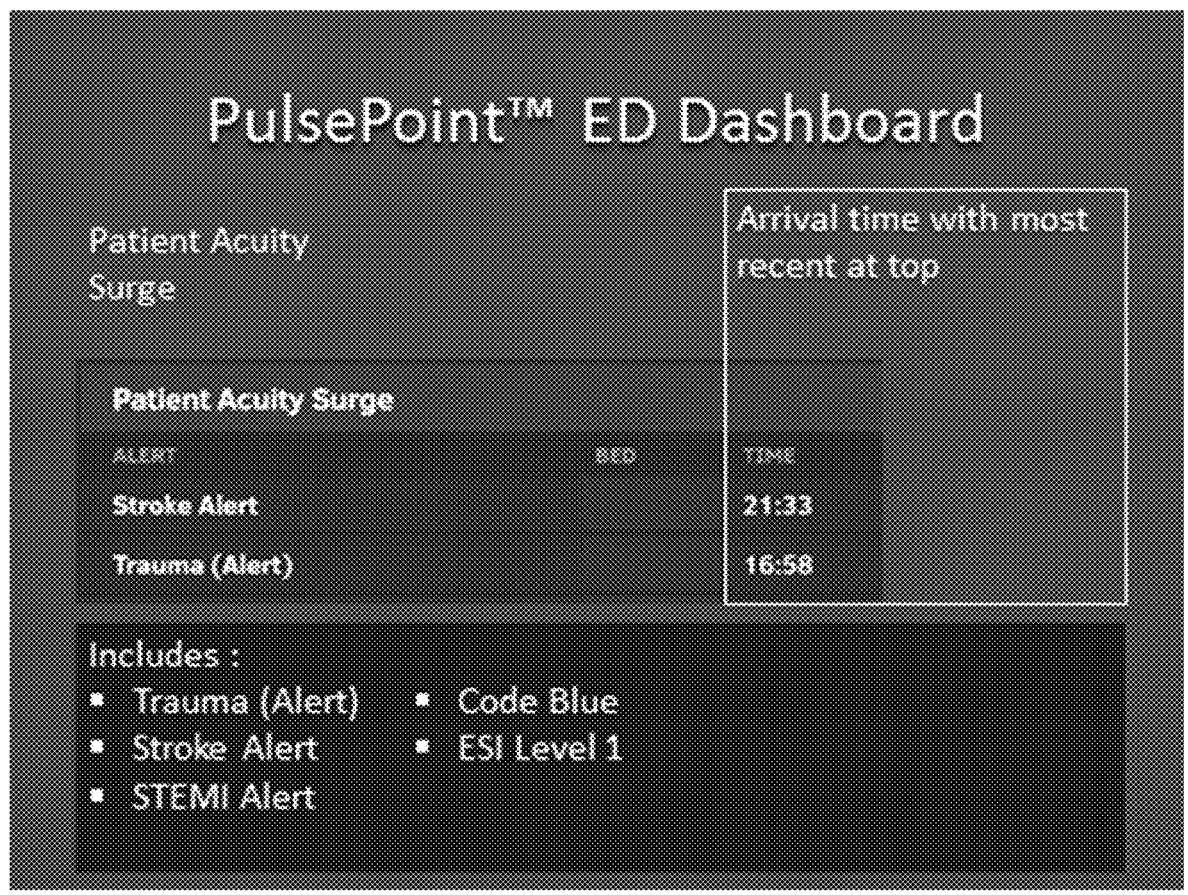
FIG. 11 illustrates a close-up view of the patient acuity surge region of the dashboard.

The dashboard also provides a count of the number of ambulances (EVAC) that have arrived in the last 60 minutes. This information is displayed in conjunction with the patient acuity surge region, which shows when the critical patients have arrived in the ED. FIG. 11 illustrates a close-up view of the patient acuity surge region of the dashboard. In this embodiment, patients with more serious conditions (e.g., trauma, stroke, STEMI, Code Blue, and/or ESI Level 1 (ESI is Emergency Severity Index and ESI 1 is the highest acuity and critically ill), are included in the patient acuity section. Each acuity alert is listed in the acuity surge region with the arrival time of each alert. This graphical dashboard provides a unified view having a combination of multiple regions that allows hospital staff to quickly assess the situation and manage ED resources.

Figure 12:
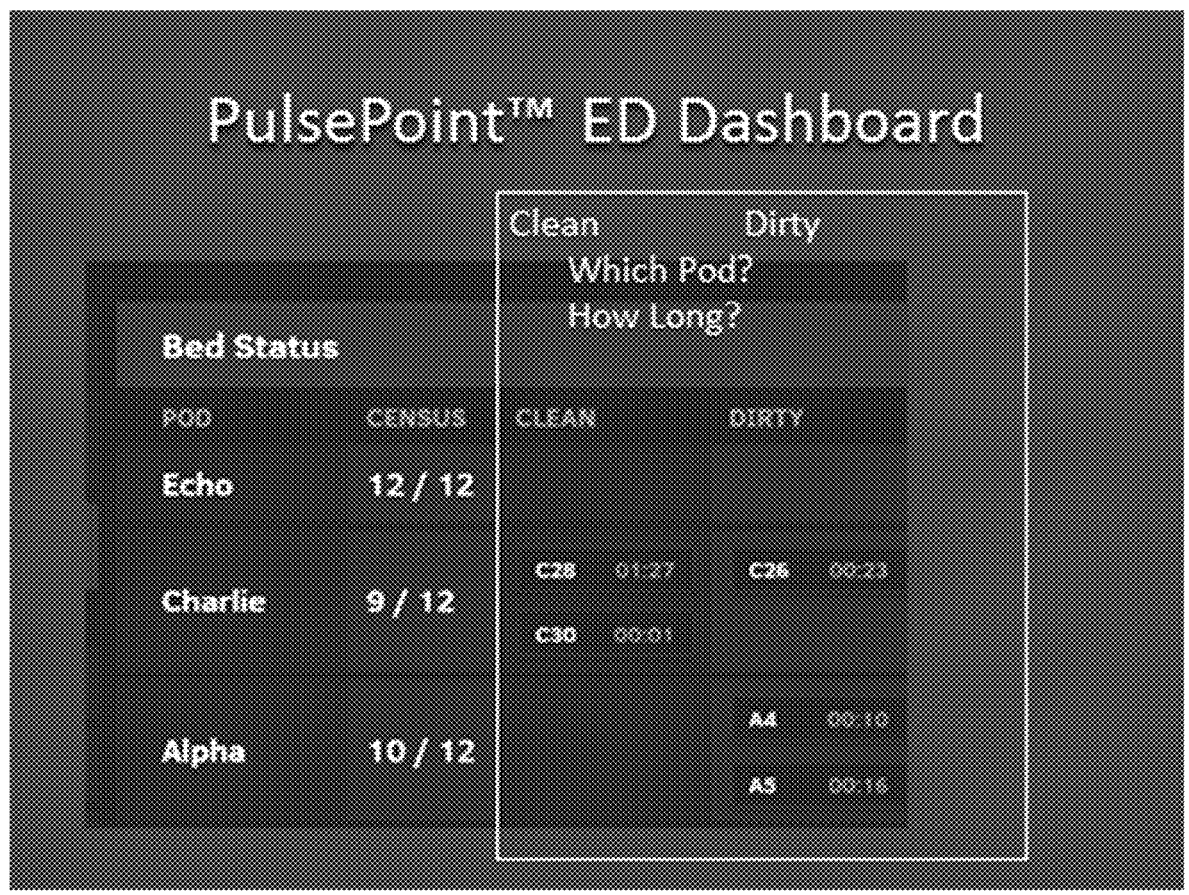
FIG. 12 illustrates one embodiment of a graphical interface illustrating bed census information along with clean and dirty bed status and time durations in each status.

Patients arriving to the emergency department need rapid placement into a bed. Some emergency departments are divided into specialized areas. In one sample hospital, the emergency department is divided into 11 areas or 11 pods, each having between 5 and 12 beds. Patients are placed in clean beds. The present invention monitors each pod's census, and bed status and the time in that status. FIG. 12 illustrates one embodiment of a graphical interface illustrating bed census information along with clean and dirty bed status and time durations in each status. The beds are each assigned a unique identifier and is displayed on the dashboard status region if they are clean or dirty. For example, in FIG. 12 bed in C pod (or Charlie pod) start with the letter "C" and are given a unique number (1-12). So, in FIG. 12, beds C28 and C30 from C pod are clean and bed C26 is dirty. Similarly, beds A4 and A5 from A pod are dirty. The duration that the bed has been in the dirty or clean status is also noted in hours and minutes (hh:mm). Bed C26 has been dirty for 23 minutes.

Figure 13:
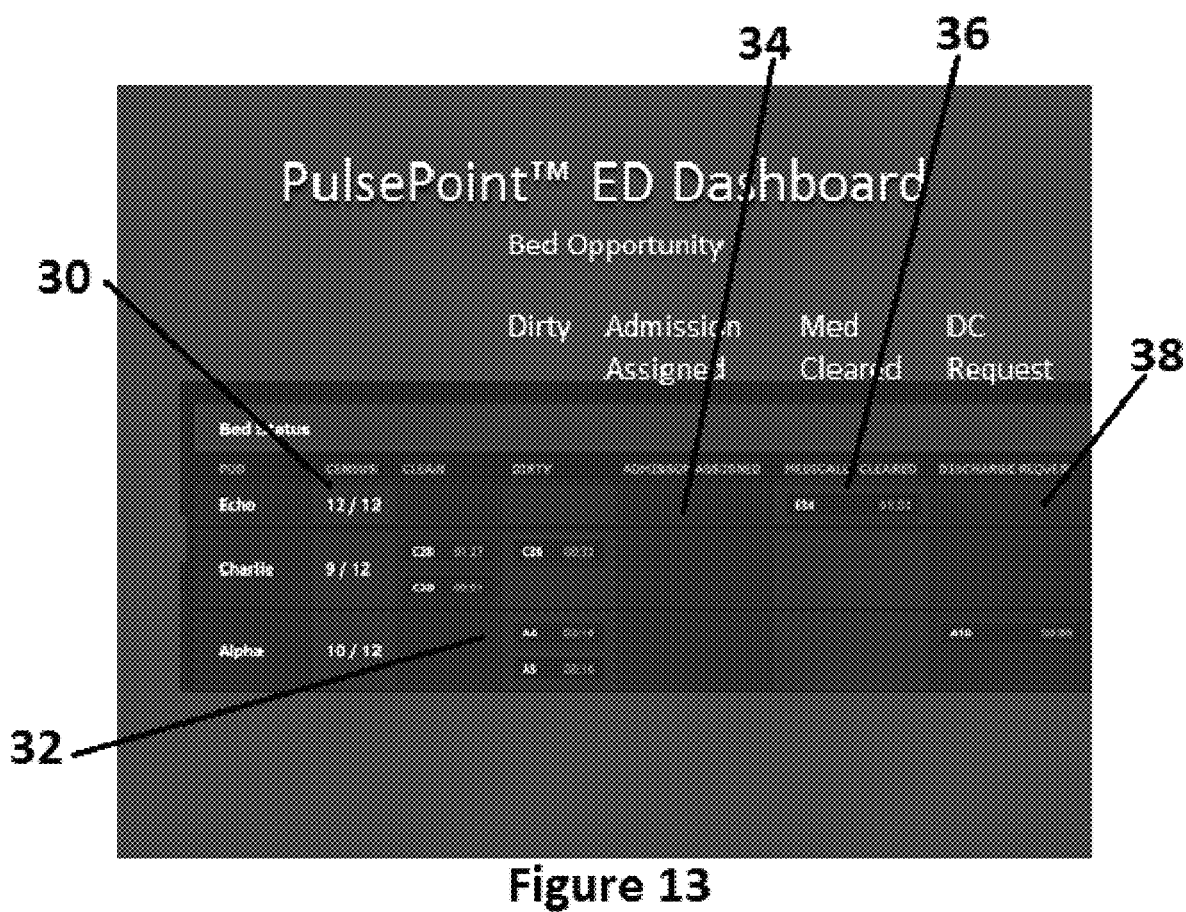
FIG. 13 illustrates one embodiment of a graphical interface providing bed census and status information along with bed opportunity data.

If no clean beds are in a desired pod, other opportunities exist to obtain a bed for waiting patients. The system is also adapted to facilitate the viewing of bed "opportunities" or situations where beds will soon be available for patients. FIG. 13 illustrates one embodiment of a graphical interface providing bed census and status information along with bed opportunity data such as beds where the patient has been assigned to admissions (and has been assigned an inpatient bed or "assigned admissions"), where the patient has been medically cleared, and where a discharge request (DC) has been written for the patient. These bed opportunities are provided for each emergency department area or pod. "Medically cleared" patients are patients who are cleared to go to the psychiatric area (or in one example J pod) of the emergency department. Alerts are sent to users regarding duration in these queues. FIG. 13 illustrates the bed census region 30, clean/dirty bed status region 32 (including time in that status), the "assigned admissions" region 34, medically cleared region 36 and pending discharge region 38. The "assigned admissions" region, the medically cleared region and the pending discharge region combine to form a "bed opportunities region" that illustrates potential beds in the ED that may be opening up. In the preferred embodiment, each pod or area of the ED has its own row in the graphical interface with each of these regions in a separate column. In other words, the admissions assigned region, medically cleared region, and pending discharge region is aligned with the bed status region so that bed status and census data for each area of the ED is aligned with the data relating to admissions assigned, medically cleared patients, and discharge requests for each area. Each area of the emergency department is displayed as a separate row in the graphical user interface with each row displaying bed census information, clean/dirty bed status and time in that status (hh:mm), admissions assigned status and time in that status, medically cleared status and time in that status, and discharge requested status and time in that status. As illustrated in the example screen shot in FIG. 13, ED area Echo (or E pod) has 12/12 bed occupied, however, bed E34 of E pod has a medically cleared patient that has been in that status for 1 hour and 1 minute (1:01). Similarly, in this example, A pod has 10/12 beds occupied however bed A10 has a patient with a discharge request status. Similarly, Charlie or C pod has two clean beds and one dirty bed. These beds provide opportunities for open beds that can be made available quickly for a patient waiting for a bed. In the present invention, beds are displayed or listed in the graphical user interface by unique bed identifiers or indicators (e.g., E34, A10, etc.). The specific interface of the present invention facilitates resource management by allowing staff to quickly view bed census and status information alongside bed opportunities. This view also allows staff to quickly determine bottlenecks in this process by reviewing the duration of time the beds have been in each of these statuses.

Figure 14:
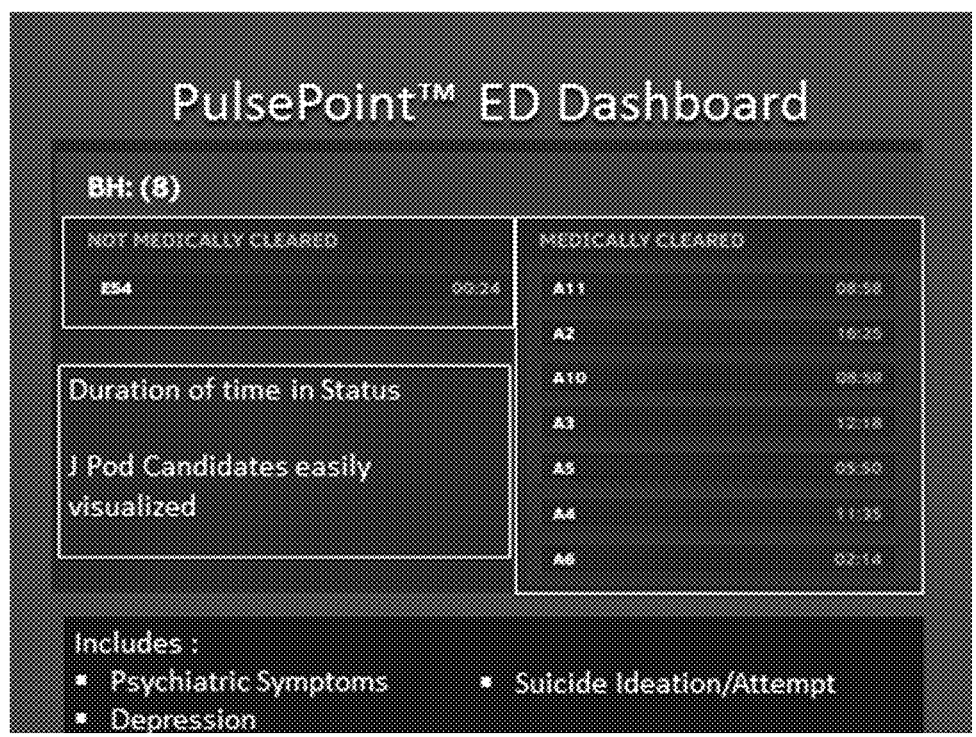
FIG. 14 illustrates one embodiment of a graphical interface having regions for showing patients in the ED that are not medically cleared, that are medically cleared, and the duration of time that each patient has been in that status.

The system also monitors the movement of behavioral health (BH) patient's movement in the emergency department. BH patients are ones with behavioral or mental health issues. BH patients are initially evaluated in an emergency department bed. After evaluation, the patients that are medically cleared are ready to be moved over to the pod dedicated as the exclusive psychiatric pod (e.g., in this embodiment, J pod). The system monitors and alerts the users in the J pod that they have medically cleared patients. The duration that the "medically cleared" patient remains outside the J pod is alerted, in an escalating fashion to users and to supervisors. FIG. 14 illustrates a portion of one embodiment of a graphical interface having regions for showing patients in the ED that are not medically cleared, that are medically cleared, and the duration of time that each patient has been in that status. Again, the beds with medically cleared patients are displayed using bed identifiers. This information is important because it allows staff to see opportunities to open up ED beds by moving the medically cleared patients to J pod.

Figure 15:
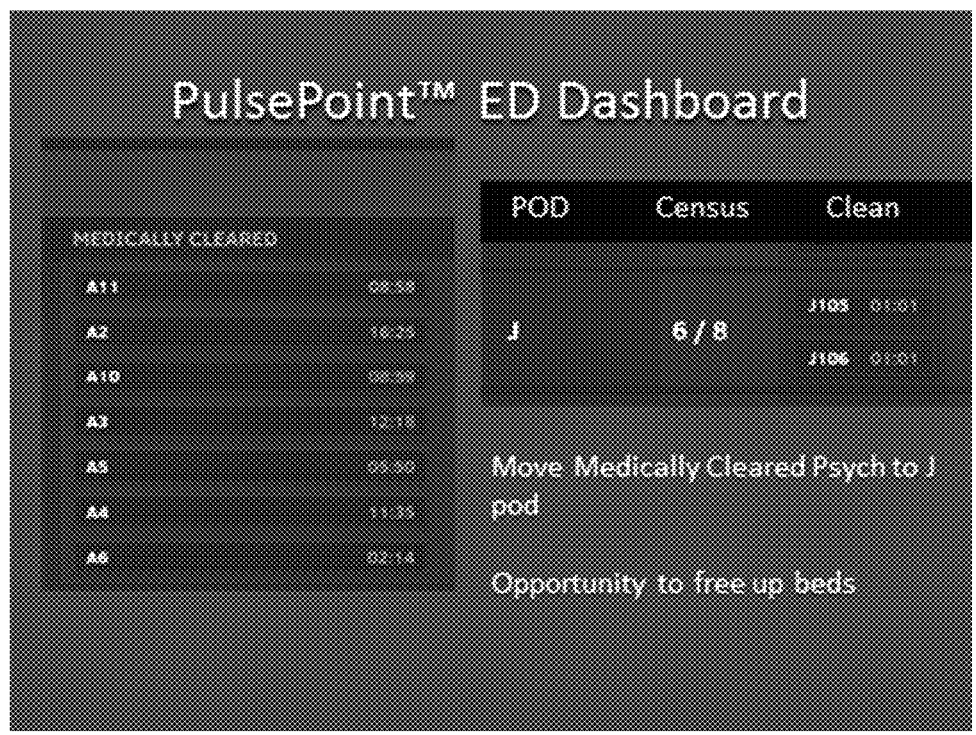
FIG. 15 illustrates an example the interplay between medically cleared patient data and bed census information from the graphical interfaces of the present invention.

FIG. 15 illustrates an example of the interplay between medically cleared patient data and bed census information from the graphical interfaces of the present invention. In the example of FIG. 15, there were 2 clean beds in J pod, each clean over an hour and 7 patients in other pods waiting to be placed in J pod, many who were medically cleared for over an hour. The system of the present invention is adapted to monitor the duration that these patients have been medically cleared and to provide alerts to the users (after a predetermined duration of time) so that the hospital staff can recognize the number of patients needing moved to J pod. The predestined amount of time is variable and based on the number of patients in the ED lobby and the duration of time in the ED lobby. In the preferred embodiment, the predestined time is less if the number of patients or the length of waiting time in the lobby is over 45 minutes. Once the staff is alerted to this condition, they can instruct others to transfer the patients or assist in the process. (See other examples discussed below.) These alerts preferably escalate (to other staff and management), based on time of day and status of the rest of the ED.

The present invention also monitors each step of the testing process of patients in the emergency department, and alerts users to the duration of the care. For laboratory tests, the user responsible for collecting specimens is notified if a specimen is not collected within 30 minutes of order. If the test is not resulted within the predetermined time limit, the lab staff is alerted to the delay. For radiologic testing, appropriate staff members are alerted if testing has not started within specified time limits. After the radiologic test is complete, the duration of time to report results is also monitored and alerts users to prolonged turnaround time.

Figure 16:
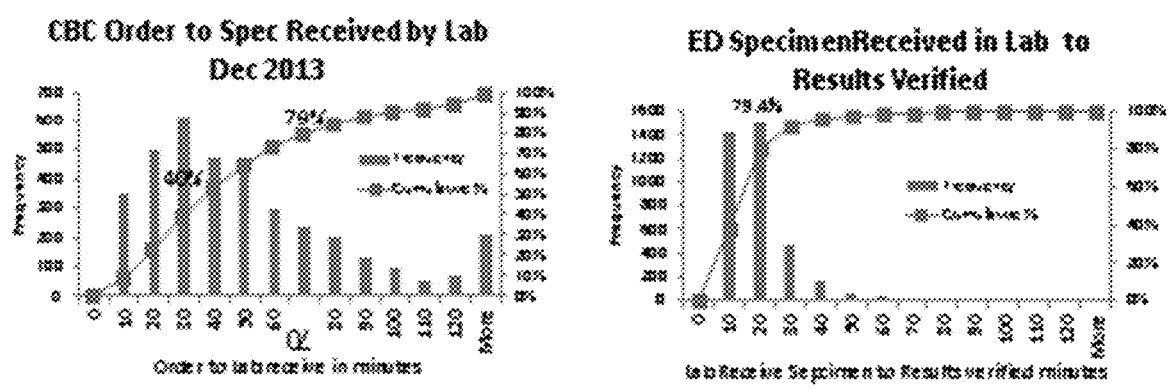
FIG. 16 provides exemplary graphs depicting variations present in the lab process, with specimen collection time having the greatest variability.

The present invention provides a unified, graphically structured interface to graphically see these admission and testing response times. FIG. 16 provides exemplary graphs depicting the variation present in the lab process, with specimen collection time having the greatest variability. The invention will monitor the specimen collection time and alert users when prolonged. The laboratory portion, which is the time when the specimen is received to test resulted, will also be monitored and the laboratory staff alerted if the process is prolonged. For example, in the below graphs, the key is to have over 80% of all lab specimens collected within 30 minutes of order. This decreases ED patient length of stay, which increases the ED's capacity, decreases LWBS and increases revenue. In the above the ED collection of specimens has the highest variability. Once the sample is in the lab, the variability in the laboratory testing time is minimal.

Figure 17:
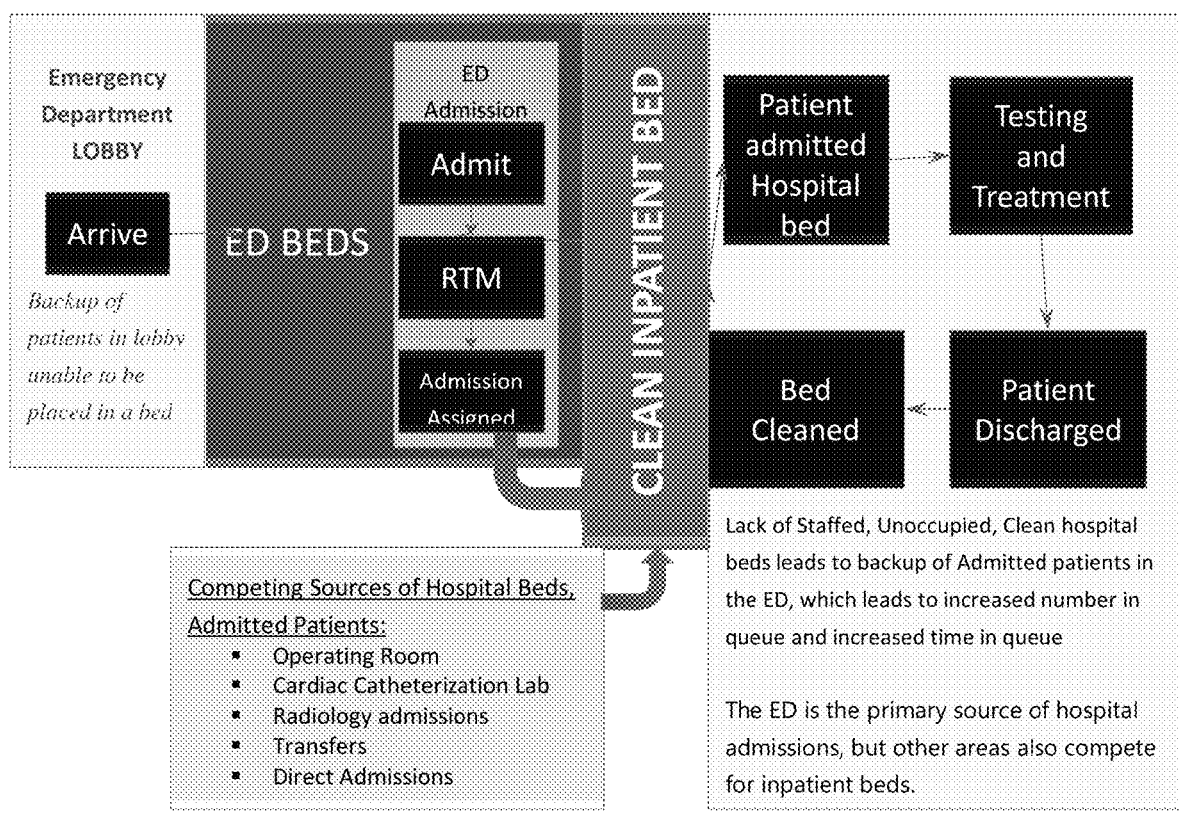
FIG. 17 illustrates a diagram of one embodiment of a hospital patient process flow showing the competition for clean beds.

FIG. 17 illustrates a diagram of one embodiment of a hospital patient process flow showing the competition for clean beds. The present invention also assists in managing incoming admissions and monitoring discharge patient flow. The system monitors queue depth and duration of:

1. Clean inpatient bed location;
2. Dirty Inpatient bed location;
3. Number of completed admissions and anticipated admissions;

The ED is calculated by looking at the average admissions per day and +/—1 Standard deviation. The daily admissions from the other departments is reported daily at a meeting (e.g., at 8:30 am).
 a. ED;
 b. Surgery;
 c. Cardiac Catheterization Lab;
 d. Radiologic department;
 e. Transfers from other hospitals;
 f. Direct admissions;
4. Discharge pending patients;
 a. Home;
 b. Home with durable medical equipment ordered;
 c. Nursing facility, skilled or unskilled;
 c. Rehabilitation facility;
 d. Hospice;
 e. Transportation services for all the above.

The present invention is also adapted to alert users to delays, and escalates to upper management based on an algorithm that is based on beds and capacity. For example, see the alert schedule in the charts below. For example, the present system is adapted to send a first alert to a first predetermined staff member if a patient has been in an admitted status (without being given a ready-to-move order) over a first predetermined length of time and to send a second alert to a second predetermined staff member (ED charge RN) if a patient has been in an admitted status over a second predetermined length of time; and to send a third alert to a third predetermined staff member (e.g., ED Assistant Medical Director) if a patient has been in an admitted status over a third predetermined length of time, etc.

As another example, the present system is adapted to send a series of escalating alerts if a patient has been in a ready-to-move status (without receiving an inpatient bed assignment) over a series of predetermined lengths of time. Similarly, the present system is adapted to send a series of escalating alerts if a patient has been in an inpatient-bed-assigned status (without being moved out of the ED) over a series of predetermined lengths of time. ("UN" stands for unit clerk and "RN" stands for registered nurse.)

| | | ESCALATION LEVEL | | |
|---|---|---|---|---|
| LOBBY ALKERTS | ED Escalation Level 1 | ED Escalation Level 2 | ED Escalation Level 3 | ED Escalation Level 4 |
| # in Lobby | 8 OR | 15 OR | 20 OR | 20 AND |
| Wait time in minutes | 45 OR | 90 OR | 120 OR | 180 |
| LWBS | 1 | 4 | 10 | |
| | Don't Alert IF: if any other lobby alert has fired in the last 15 minutes | Don't Alert IF: if any other level 2, 3 or 4 lobby alert has fired in the last 15 minutes | Don't Alert IF: if any other level 3 or 4 lobby alert has fired in the last 15 minutes | Don't Alert IF: None |
| ED RNs | ED Escalation Level 1 | ED Escalation Level 2 | ED Escalation Level 3 | |
| ED TECH5 | ED Escalation Level 1 | ED Escalation Level 2 | ED Escalation Level 3 | |
| ED Charge RN | ED Escalation Level 1 | ED Escalation Level 2 | ED Escalation Level 3 | |
| ED Clinical Coordinators | ED Escalation Level 1 | ED Escalation Level 2 | ED Escalation Level 3 | |
| ED RN manager | | ED Escalation Level 2 | ED Escalation Level 3 | ED Escalation Level 4 |
| ED Assistant Medical | | | ED Escalation | ED Escalation |

-continued

| | | Level 3 | Level 4 |
|---|---|---|---|
| Director | | ED | ED |
| ED Medical | | Escalation | Escalation |
| Director | | Level 3 | Level 4 |
| House | | ED | ED |
| Supervisor | | Escalation | Escalation |
| | | Level 3 | Level 4 |
| Floor Charge | | ED | ED |
| RN | | Escalation | Escalation |
| | | Level 3 | Level 4 |
| Floor UC | | ED | ED |
| | | Escalation | Escalation |
| | | Level 3 | Level 4 |
| Floor Unit | | ED | ED |
| Managers | | Escalation | Escalation |
| | | Level 3 | Level 4 |
| CNO | | ED | ED |
| | | Escalation | Escalation |
| | | Level 3 | Level 4 |
| COO | | ED | ED |
| | | Escalation | Escalation |
| | | Level 3 | Level 4 |
| CEO | | | ED |
| | | | Escalation |
| | | | Level 4 |

| | Alert | | | |
|---|---|---|---|---|
| Dirty Bed Alerts | Dirty Bed level 0 | Dirty Bed level 1 | Dirty Bed level 2 | Dirty Bed level 3 |
| Dirty Bed | Each time | >15 min dirty | >20 min dirty | 3 or more beds dirty for 30 min |
| Other Conditions | AND None | AND Lobby 1 | AND Lobby 2,3, or 4 | AND Lobby 3 |
| Exceptions | Don't Alert IF: None | Don't Alert IF: None | Don't Alert IF: None | Don't Alert IF: None |
| Housekeeper in ED assigned to pod | Dirty Bed level 0 | | | |
| ED Tech Assigned to Pod | | Dirty Bed level 1 | | |
| ED EVS Supervisor | | | Dirty Bed level 2 | Dirty Bed level 3 |
| EVS Manager | | | | Dirty Bed level 3 |

| | ADMISSION ALERTS | | | Level Admission Decision to Admit Level 0 | |
|---|---|---|---|---|---|
| ED Admission Alert-Decision to Admit | | | | Each time | |
| UC in Pod | | | | Admission Decision to Admit Level 0 | |

| | Level | | | | |
|---|---|---|---|---|---|
| | Admit no RTM Level 0 | Admit no RTM Level 1 | Admit no RTM Level 2 | Admit no RTM Level 3 | Admit no RTM Level 4 |
| ED Admission Alerts-Admit no RTM | >60 minutes form decision to Admit | >30 minutes form decision to Admit | >90 minutes from Decision to admit, no RTM | >90 minutes from Decision to admit, no RTM | >120 minutes from Decision to admit, no RTM |
| | and | and | AND | AND | AND |

-continued

|  | | | | | |
|---|---|---|---|---|---|
| Other conditions | None | Lobby Alert 1,2,3,4 | Lobby Alert 1,2,3,4 | Lobby Alert 2,3,4 | Lobby Alert 2,3,4 |
| | | Don't Alert IF: | Don't Alert IF: | Don't Alert IF: | Don't Alert IF: |
| Exceptions | None | None | None | NONE | NONE |
| UC in Pod | | Admit no RTM Level 0 | Admit no RTM Level 1 | Admit no RTM Level 2 | Admit no RTM Level 4 |
| ED Charge RN | | | | Admit no RTM Level 2 | Admit no RTM Level 4 |
| ED Assistant Medical Director | | | | Admit no RTM Level 3 | |
| CMO | | | | | Admit no RTM Level 4 |

| | Level | | | |
|---|---|---|---|---|
| | Admit RTM, no bed level 0 | Admit RTM, no bed level 1 | Admit RTM, no bed level 2 | Admit RTM, no bed level 3 |
| ED Admission Alerts-Admit and RTM, No bed Assignment | Any Admitted patients with RTM | Any Admitted patients with RTM | over 4 Admitted patients with RTM | 10 Admitted patients with RTM |
| | And | And | And | And |
| Other conditions | Any Lobby Alert | Lobby Alert 2-4 | Lobby Alert 2-4 | Lobby Alert 3,4 |
| | Don't Alert IF: | Don't Alert IF: | Don't Alert IF: | Don't Alert IF: |
| Exceptions | None | This alert sent out in the last 30 minutes. | This alert sent out in the last 30 minutes. | This alert sent out in the last 60 minutes. |
| Bed Scheduling | Admit RTM, no bed level 0 | | | |
| Floor UC | | Admit RTM, no bed level 1 | | |
| Floor Charge RNs | | Admit RTM, no bed level 1 | | |
| Floor RN Managers | | | Admit RTM, no bed level 2 | Admit RTM, no bed level 3 |
| Director of Med-Surg units | | | Admit RTM, no bed level 2 | Admit RTM, no bed level 3 |
| House Supervisor | | | Admit RTM, no bed level 2 | Admit RTM, no bed level 3 |
| Director of Med-Surg units | | | Admit RTM, no bed level 2 | Admit RTM, no bed level 3 |
| Director of ICUs | | | Admit RTM, no bed level 2 | Admit RTM, no bed level 3 |
| Director of PACU | | | Admit RTM, no bed level 2 | Admit RTM, no bed level 3 |
| Director of Bed Scheduling | | | | Admit RTM, no bed level 3 |
| CNO | | | | Admit RTM, no bed level 3 |

| | Level | | | |
|---|---|---|---|---|
| | Admit Assigned Level 0 | Admit Assigned Level 1 | Admit Assigned Level 2 | Admit Assigned Level 3 |
| ED Admission Alert-Admit Assigned | Each time | pt. remains in ED > 30 after bed assigned | pt. remains in ED > 60 after bed assigned | |

-continued

| | | | | |
|---|---|---|---|---|
| Other conditions | And None | And None | And Lobby Alert 2-4 | And None |
| Exceptions | Don't Alert IF: | Don't Alert IF: | Don't Alert IF: | Don't Alert IF: |
| ED RN Assigned to Bed | Admit Assigned Level 0 | Admit Assigned Level 1 | Admit Assigned Level 2 | |
| Floor RN Assigned to Bed | Admit Assigned Level 0 | Admit Assigned Level 1 | Admit Assigned Level 2 | |
| ED Charge RN | | Admit Assigned Level 1 | Admit Assigned Level 2 | |
| Floor charge RN receiving pt. | | Admit Assigned Level 1 | Admit Assigned Level 2 | |
| Observation Charge RN | | Admit Assigned Level 1 | Admit Assigned Level 2 | |
| Observation RN Manager | | Admit Assigned Level 1 | Admit Assigned Level 2 | |
| Floor RN Manager | | | Admit Assigned Level 2 | |
| ED RN Manage | | | Admit Assigned Level 2 | |

| | | | Level | | |
|---|---|---|---|---|---|
| Behavioral Health ALERTS | Psych Alert Level 0 | Psych Alert Level 1 | Psych Alert Level 2 | Psych Alert Level 3 |
| BH Alert | Medically Cleared BA in Pods A,C,E | Medically Cleared Baker Acts in Pods A,C,E for over 30 minutes | Medically Cleared Baker Acts in Pods A,C,E | J Pod Full and Medically cleared BA in Pods A, B, C, D, E |
| Other conditions | And | And Unoccupied beds in J Pod | And Lobby Alert 2-4 | And Lobby Alert 2-4 |
| Other conditions | And None | And None | And None | And all J Pod beds occupied |
| Exceptions | Don't Alert IF: Level 3 or 4 Alert Sent in last 20 minutes | Don't Alert IF: Level 3 or 4 Alert Sent in last 20 minutes | Don't Alert IF: None | Don't Alert IF: None |
| J pod UC | Psych Alert Level 0 | Psych Alert Level 1 | Psych Alert Level 2 | |
| J Pod RN | Psych Alert Level 0 | Psych Alert Level 1 | Psych Alert Level 2 | |
| J POD Supervisor | | Psych Alert Level 1 | Psych Alert Level 2 | |
| Psych Supervisor | | | Psych Alert Level 3 | |

| | | | Level | | |
|---|---|---|---|---|---|
| ED DISCHARGE ALERTS | ED Discharge level 0 | ED Discharge level 1 | ED Discharge level 2 | ED Discharge level 3 |
| ED Bed Alert- ED Discharge | Each Time | pt. remains in ED > 30 after Discharge | pt. remains in ED > 45 after Discharge | |
| | | And | And | And |

-continued

|  |  |  |  |
|---|---|---|---|
| Other conditions | None | any lobby alert | any lobby alert |
|  | Don't Alert IF: | Don't Alert IF: | Don't Alert IF: |
| Exceptions | None | None | None |
| ED RN Assigned to Bed | ED Discharge level 0 | ED Discharge level 1 |  |
| ED Charge RN |  | ED Discharge level 1 | ED Discharge level 2 |
| ED Clinical Coordinators |  |  | ED Discharge level 2 |

| | Level | | |
|---|---|---|---|
| Lab Delay Alerts | Draw Delay level 1 | | Draw Delay level 2 |
| ED lab draw Alert | >30 min from lab order to lab draw And | | >60 min from lab order to lab draw |
| Other conditions | None | | None |
|  | Don't Alert IF: | | Don't Alert IF: |
| Exceptions | None | | None |
| ED RN Assigned to Bed | Draw Delay Bed __ | | Draw Delay Bed __ |
| ED Charge RN |  | | Draw Delay Bed __ |
| ED Clinical Coordinators |  | | Draw Delay Bed __ |

| | Level | | |
|---|---|---|---|
| Lab Delay Alerts | Lab Results Delay level 1 | Lab Results Delay level 2 | Lab Results Delay level 3 |
| ED lab Result Alert | >20 min from lab specimen receive to lab result for selected lab And | >40 min from lab specimen receive to lab result for selected lab | >60 min from lab specimen receive to lab result for selected lab |
| Other conditions | None | None | None |
|  | Don't Alert IF: | Don't Alert IF: | Don't Alert IF: |
| Exceptions | None | None | None |
| Lab Tech assigned to instrument | Result Delay in Chemistry or Hematology or Coags or Urinalysis |  |  |
| Lab Supervisor |  | Result Delay in Chemistry or Hematology or Coags or Urinalysis |  |
| Lab Manager |  |  | Result Delay in Chemistry or Hematology or Coags or Urinalysis |

-continued

| Radiology Delay Alerts Plain Radiography | Radiology Test Start Delay level 1 | Radiology Test Start Delay level 2 | Radiology Test Start Delay level 3 |
|---|---|---|---|
| | Level | | |
| ED Plain Radiograpy Order to Test Start | >20 min | >40 min | >60 |
| Other conditions | And None | None | None |
| Exceptions Xray Tech Assigned to ED | Don't Alert IF: None Xray Delay bed __ | Don't Alert IF: None | Don't Alert IF: None |
| Xray Supervisor | | Xray Delay bed __ | |
| Radiology Manager | | | Xray Delay bed __ |

| Radiology Delay Alerts Non Contrast CT | Radiology Test Start Delay level 1 | Radiology Test Start Delay level 2 | Radiology Test Start Delay level 3 |
|---|---|---|---|
| | Level | | |
| ED Non-Con CT Order to Test Start | >20 min | >40 min | >60 |
| Other conditions | And None | None | None |
| Exceptions CT Tech Assigned to ED | Don't Alert IF: None CT Delay bed __ | Don't Alert IF: None | Don't Alert IF: None |
| CT Supervisor | | CT Delay bed __ | |
| Radiology Manager | | | CT Delay bed __ |

| Radiology Test Delay Alerts ED Contrast CT | Radiology Test Start Delay level 1 | Radiology Test Start Delay level 2 | Radiology Test Start Delay level 3 |
|---|---|---|---|
| | Level | | |
| ED Contrast CT Order to Test Start | >60 min | >92 min | >120 |
| Other conditions | And None | None | None |
| Exceptions CT Tech Assigned to ED | Don't Alert IF: None CT Delay bed __ | Don't Alert IF: None | Don't Alert IF: None |
| CT Supervisor | | CT Delay bed __ | |
| Radiology Manager | | | CT Delay bed __ |

-continued

| Radiology Results Delay Alerts All Studys | Radiology Test Result Delay level 1 | Radiology Test Start Delay level 2 | Radiology Test Result Delay level 3 |
|---|---|---|---|
| ED Non-Con CT Order to Test Start | >30 min | >45 min | >90 |
| Other conditions | And None | None | None |
| Exceptions Radiologist on call | Don't Alert IF: None Radiology Results delay | Don't Alert IF: None | Don't Alert IF: None |
| Radiology medical director | Radiology Results delay | | |
| Chief Medical Officer | | | Radiology Results delay |

Figure 18:
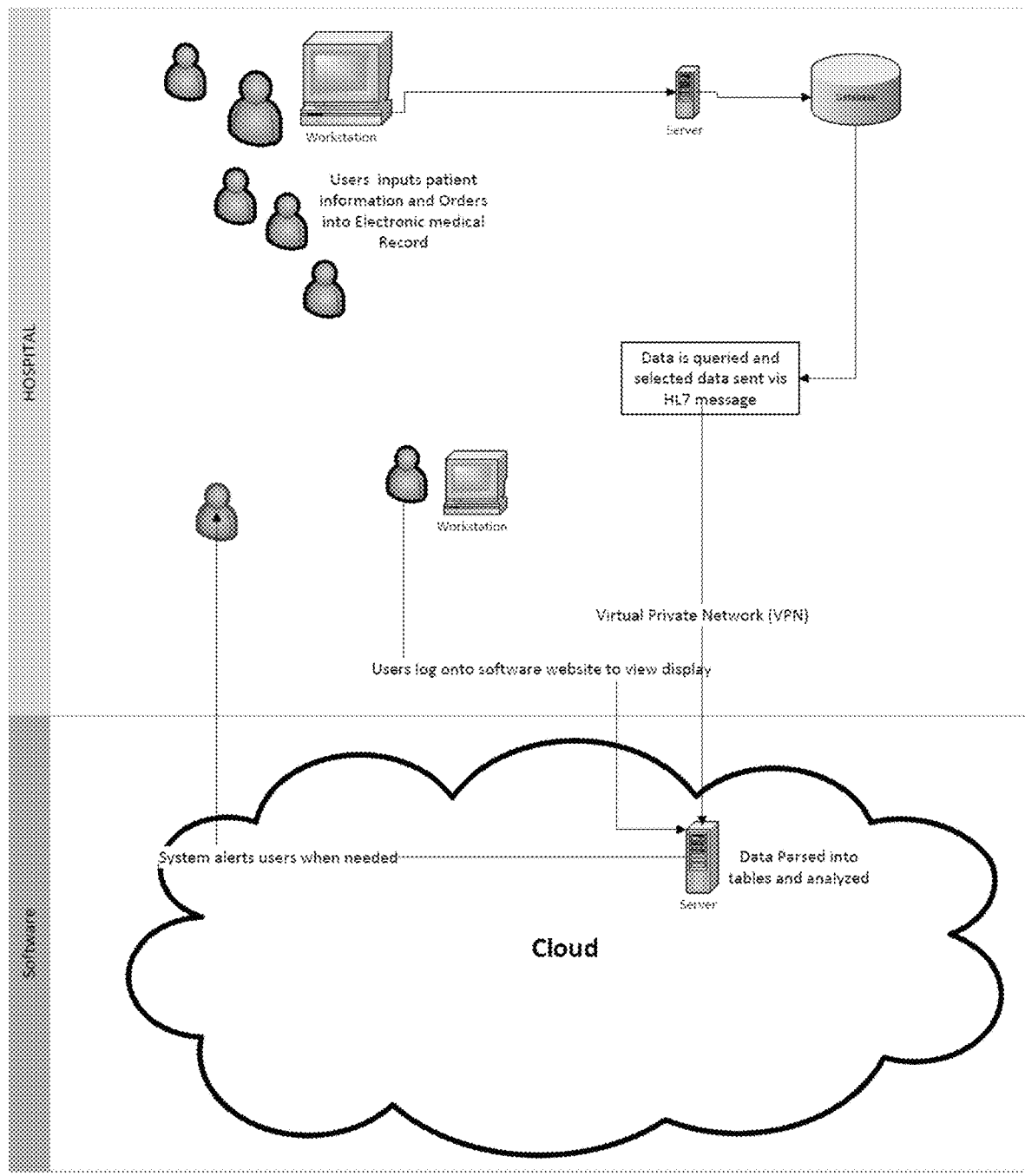
FIG. 18 illustrates one embodiment of the system diagram of one embodiment of the invention.

FIG. 18 illustrates one embodiment of the system diagram of one embodiment of the invention. In this embodiment, patient information and orders are inputted via a server into a database. This data is retrieved and sent an HL7 message over a network connection to another server (e.g., located in a cloud system). Users of the system of the present invention can then log into the cloud-based server to view the graphical user interface of the present invention. The cloud-based server is also adapted to provide alerts to users or staff as previously discussed.

The following examples represent ways that various hospital staff can use the present invention, including the specifically structured graphical interface to remove bottlenecks, allocate open resources (e.g., beds), manage staffing, and improve patient process flow in the hospital.

Triage Nurse—can use the present invention to quickly find a bed for patients coming into the ED by viewing the graphical interface to determine:
1. location of clean beds;
2. location of dirty beds.

If the triage nurse needs a bed for a critical patient, the nurse can call the person in charge of the dirty bed and have it cleaned immediately.

Charge Nurse—can use the present invention to manage the admissions flow and BH (psych patients) flow by viewing the graphical interface to determine:
1. is the ED lobby backed up by looking at the total number of patients waiting in the lobby (combination of patients awaiting triage and the patients awaiting a bed). The staff can also look at the region indicating the patient having the longest lobby wait time (historically patients start leaving the ED department without being seen (LWBS) if they have to wait more than 45 minutes).
2. Admissions Assigned (admitted patients with assigned inpatient beds)—how long have they been in this status? The nurses have a goal of transporting admitted assigned patient to the floor within 30 minutes of bed assignment. The charge nurse can assist in mobilizing other staff to help transport the patient if the nurse is busy and cannot report to the nurse who is receiving the patient.
3. BH patients medically cleared—is there clean or dirty J pod beds that the patient can be moved into?
4. Is there a surge of arriving patients? Are there a lot of seriously ill or hurt patients (acuity surge)? Is there a need to ask the nurse manager to call in staff?

Flow Nurse—can use the present invention to manage the flow of patients through the ED.
1. Is the ED lobby backed up?
2. Are their patients waiting in the ED lobby and dirty beds in the ED that need cleaned?
3. Admissions Assigned—how long have they been in this status—can the charge nurse help move the patients out of the emergency room to the inpatient bed?
4. Can the medically cleared BH patients be moved to their rooms quicker?

ED Nurse Manager—can use the present invention to determine how the ED is operating and does the ED nurse manager need to intervene?
1. Is the ED lobby backed up? If so, what is the reason? Is it due to patient volume surge, acuity surge or both? If none of the above, are the beds being utilized fully? Are there clean or dirty beds that are unoccupied?
2. How many LWBS?

CNO or COO—can use the present invention to determine how the ED is operating and does the ED nurse manager need to intervene?
1. Is the ED lobby backed up? If so, what is the reason?
2. LWBS?
3 Surge? Is there a need to add resources?
4. Is there a backup or bottleneck in the admissions process (for example, patients remaining in the bed request status for too long, patients remaining in the "ready-to-move" status for too long; and or patients remaining in the "inpatient bed assigned" status for too long)? Is there a need to intervene and open additional overflow beds in the hospital?

Figure 19:
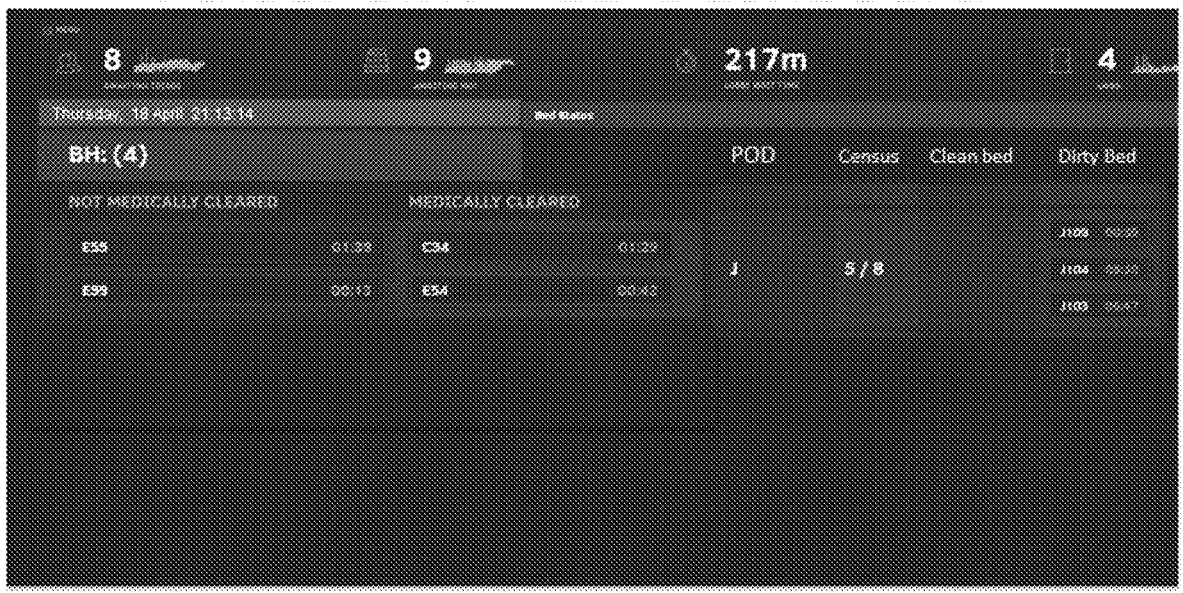
FIG. 19 illustrates one example dashboard screen illustrating one emergency department scenario.

FIG. 19 illustrates one example dashboard screen illustrating one emergency department scenario. In this scenario, the graphical user interface shows that there are 17 patients in the emergency department lobby (9 have seen a triage nurse and are awaiting to be placed in a bed, 8 haven't been triaged). All the ED beds are full with patients.

Figure 20:
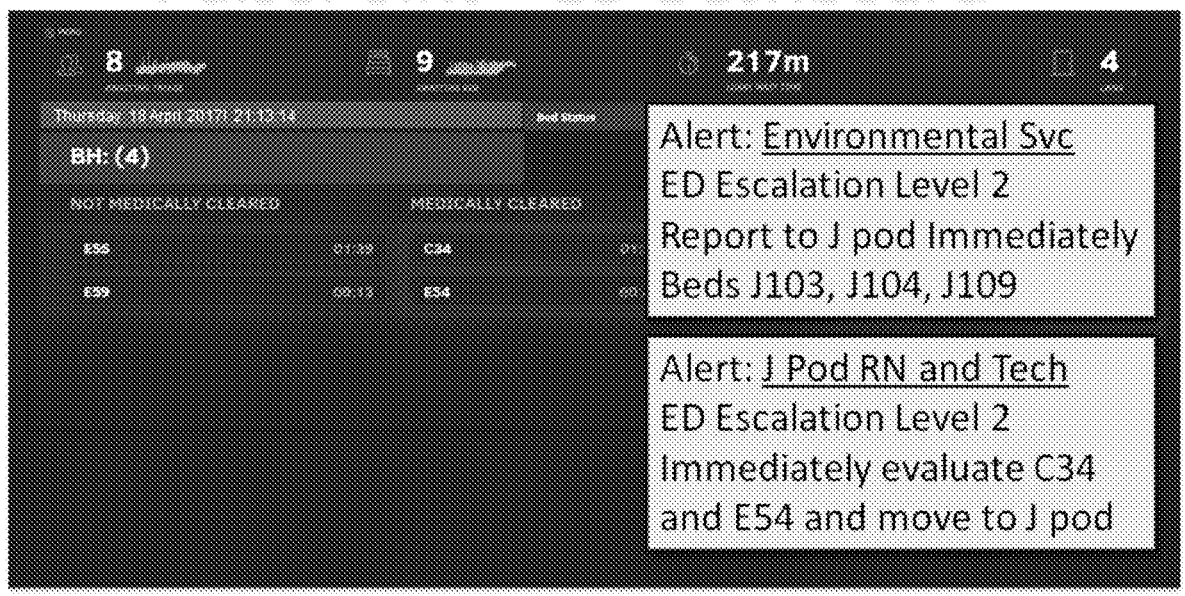
FIG. 20 illustrates alerts generated by the example illustrated in FIG. 19.

FIG. 20 illustrates alerts generated by the example illustrated in FIG. 19. In this example, a Level 2 alert is sent to a first predetermined group of staff members because the system senses that there are medically cleared patients waiting for a bed, yet there are three beds in J Pod that are dirty and need to be cleaned, and that patients in beds C34 and E54 need to be moved to J Pod.

Figure 21:
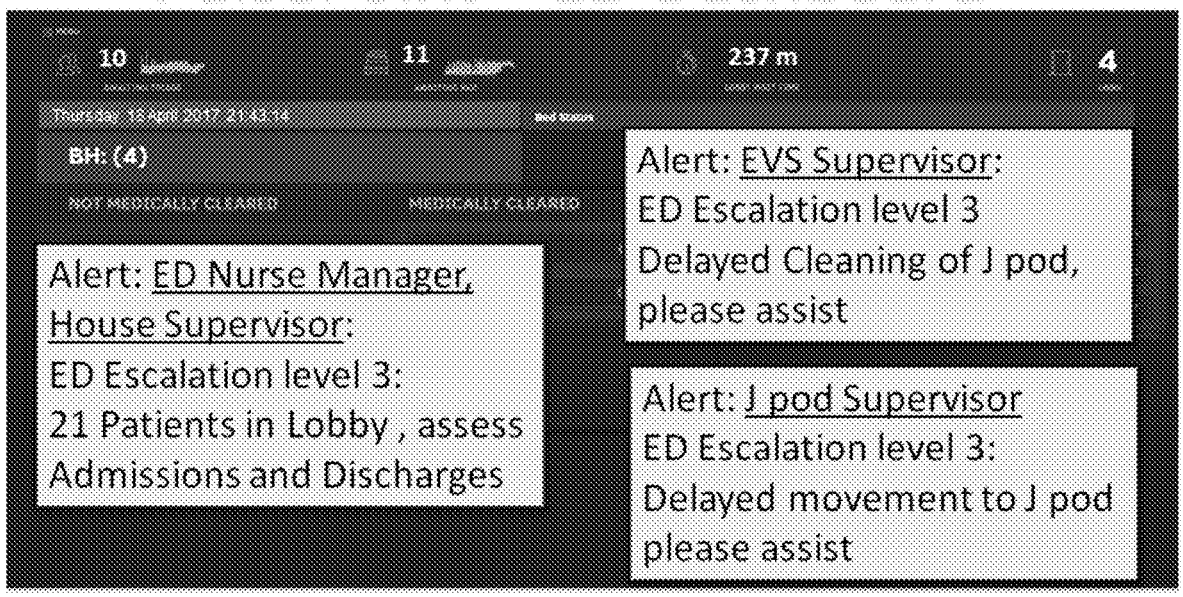
FIG. 21 illustrates subsequent alerts generated by the example illustrated in FIG. 19.

FIG. 21 illustrates subsequent alerts generated by the example illustrated in FIG. 19. In this illustration, the scenario of FIG. 19 has become worse. The lobby wait time has grown to 237 minutes and there are now 21 patients waiting in the lobby of the emergency room. In this example, a Level 3 alert is sent to a second predetermined group of staff members (different from the first, e.g. ED Nurse Manager, House Supervisor, EVS Supervisor, J Pod Supervisor) to provide an alert of the problem and that it should be fixed.

Figure 22:
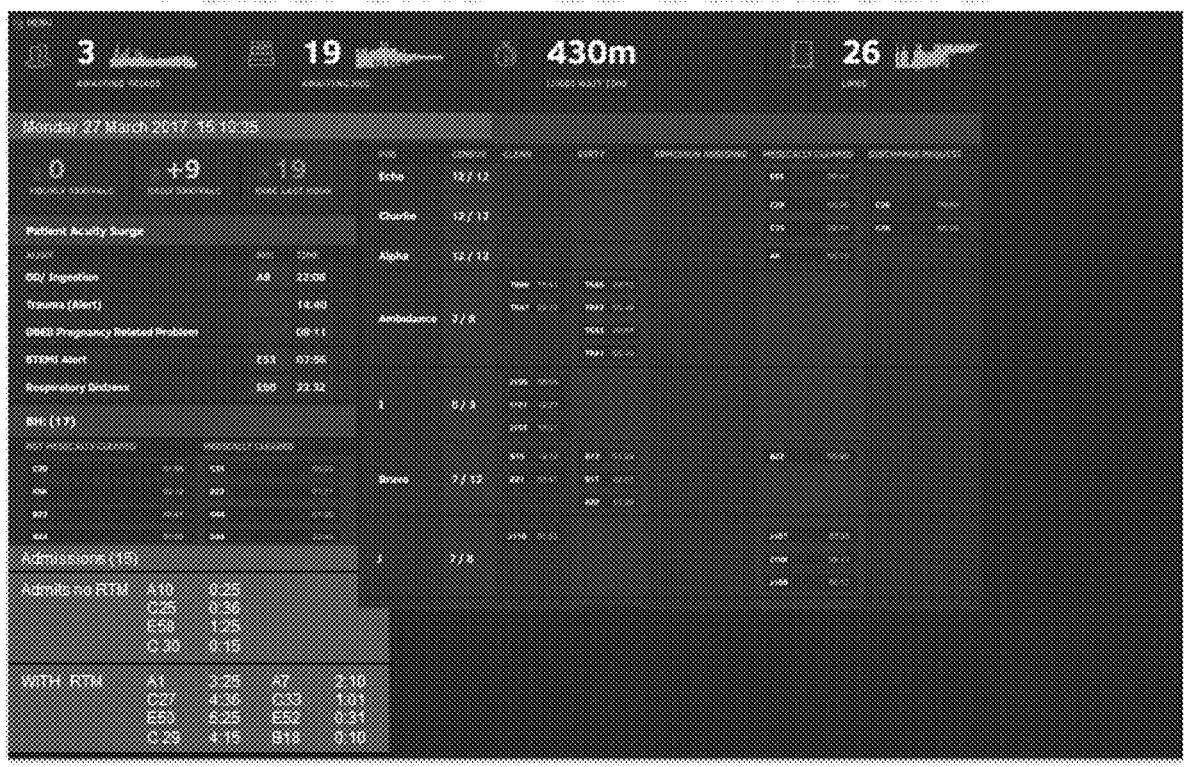
FIG. 22 illustrates one example of another embodiment of the graphical user interface or dashboard of the present invention illustrating a hospital admissions region illustrating a list of patients in the emergency room that have been cleared for admissions.

FIG. 22 illustrates one example of another embodiment of the graphical user interface or dashboard of the present invention illustrating a hospital admissions region illustrating a list of patients in the emergency room that have been cleared for admissions. Some of these patients have a request to move (RTM) order and some do not. In this scenario, at 3:10 pm on a Monday. ED Lobby is backing up with 22 patients and a long lobby wait time. 26 patients have already LWBS. The ED is busier than normal, with an additional 9 patients above average arriving that historical averages (+9). The ED beds in Alpha, Charlie and Echo are full and 2 patients are on the ambulance wall (beds in a unit dedicated to ambulance patients). 12 ED beds are full of patients cleared for admissions, with 8 having assigned a RTM (the admissions regions lists each patient with the time duration they have been in that status). The "admissions assigned" in the bed opportunities region is currently empty because none of the patients cleared for admissions have been assigned a hospital bed.

Figure 23:
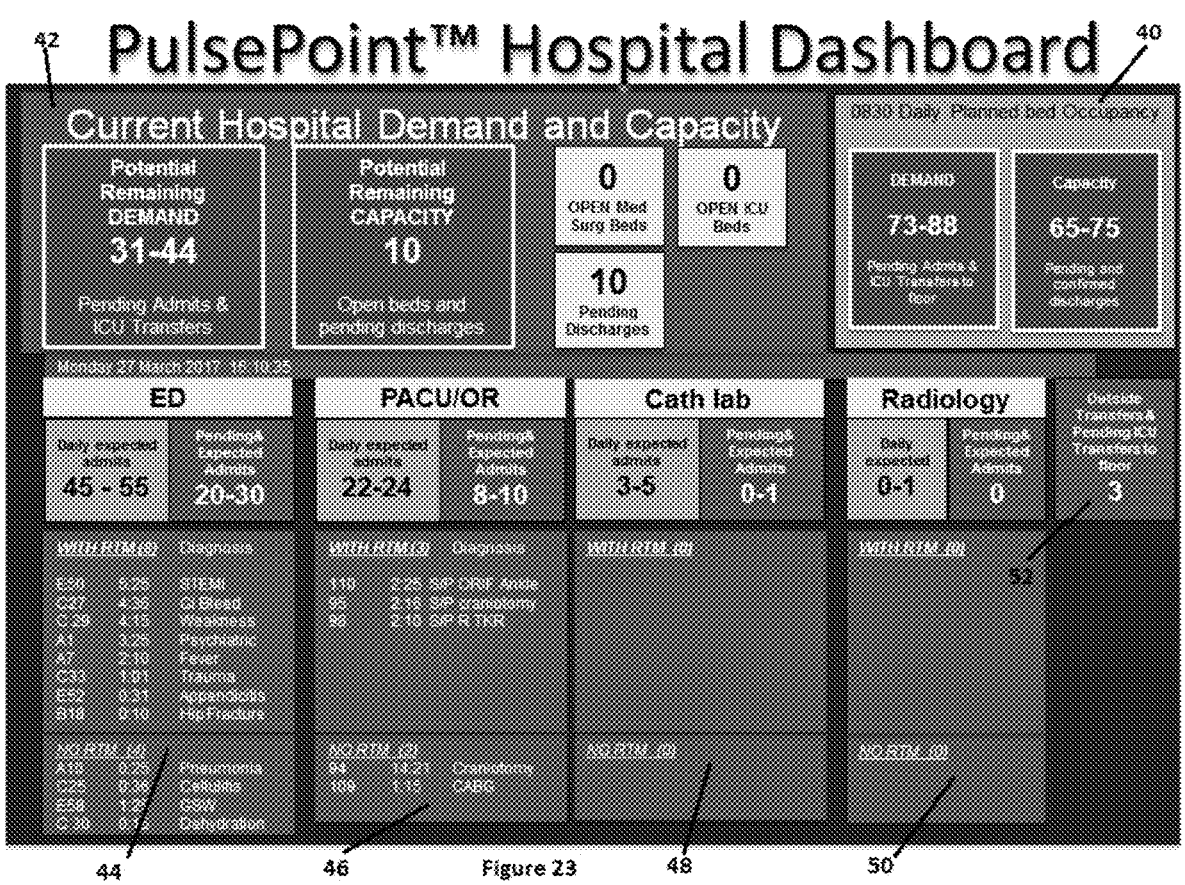
FIG. 23 illustrates one example of a hospital dashboard graphical user interface of the present invention illustrating admissions demand versus capacity.

FIG. 23 illustrates one example of a hospital dashboard graphical user interface of the present invention illustrating admissions demand versus capacity and another example scenario for a hospital. In this example, the hospital board (or designated group of hospital staff members) meets at 08:30 each day or when the daily bed meeting occurs. The daily expected patient admissions (expected admits) are reported by each of the admitting areas as well as ICU transfers and these numbers are displayed in the hospital dashboard in regions designated for each admitting area. The daily expected demand or admits for the emergency department is preferably determined using historical averages (e.g., daily average for the last year). The daily expected demand for the other admitting areas are preferably determined by scheduled admissions for each area. ("PACU" stands for post anesthesia care unit or the area patients are sent after surgery). The total expected admits is inputted manually or electronically into the hospital system and graphically displayed in the GUI in a daily planned bed occupancy region 40 (e.g., daily bed demand). This region also contains the daily planned bed capacity and/or expected total patient discharges.

In the preferred embodiment, the hospital dashboard also has a current hospital demand and capacity region 42 in the same screen as the daily planned bed occupancy region. The current hospital demand and capacity region shows the pending and expected admits known and expected for the current time of day. For example, the potential remaining demand is the sum of the pending and expected admissions for each admitting area for the current time of day. The potential remaining demand for each admitting area is also depicted in the GUI. In the preferred embodiment, the potential remaining demand for each admitting area is shown next to the daily expected admits for each admitting area (in regions designated for each admitting area, ED 44, PACU 46, Cath lab 48, Radiology 50, ICU transfers 52). For example, in the FIG. 23, at 3:10 pm, the ED department is showing a potential demand of between 20-30 patients, the PACU/OR departments is showing a potential demand of between 8-10 patients, the Cath lab is showing a potential demand of between 0-1 patients, the Radiology department is showing a potential demand of 0 patients, and the hospital is expecting 3 transfers from the intensive care unit (ICU). The total of each of these potential demands is added together and shown in the current hospital demand and capacity region as the potential remaining demand of 31-44 patients.

In another embodiment, potential patient demand represents just the pending patient admissions (excluding expected admissions). In this embodiment, the potential remaining capacity represents open beds or the sum of the open beds and pending discharges. As illustrated in FIG. 23, the hospital dashboard can also include indicators for indicating the number of open beds such as surgical beds, ICU beds, as well as listing pending discharges for the current time of day.

In the preferred embodiment, the pending admissions for each admitting area are listed for each admitting area respectively (in the regions designated for each admitting area) by bed number, duration of time in the bed, and by diagnosis. For example, in the example of FIG. 23, at 3:10 pm there are 12 pending patient admissions in the ED (8 of the patients have RTM order, 4 do not). The depiction of the diagnosis in the GUI is helpful for hospital staff to ascertain what area of the hospital the patient will be assigned to.

The software assists management to know if additional staff or beds are needed. For example, one option for beds is to keep PACU open for an extended period of time, especially if hospital discharges are delayed or taking longer than expected (the PACU normally closes down at 7 PM in typical hospitals). In the example of FIG. 23, the hospital is over capacity by 21-34 beds. Looking at the ED dashboard, the ED is over capacitated with many patients waiting in the lobby and the arrivals are above capacity. There are currently 12 ED Admissions. Accordingly, in the present example, the system provides the following assessment and alerts:

Software Assessment:
    Hospital Bed Demand>Hospital bed capacity at 15:10.
    ED Bed Demand>ED bed capacity.
    High LWBS.
    Above average arrivals.
Software Prescriptive Action:
    Open Overflow beds and/or Retain PACU staff.
    Hospital Surge Plan level 2.
    ALERT CNO, COO, Hospital Supervisor.
    Alerts all hospital staff of status.

Figure 24:
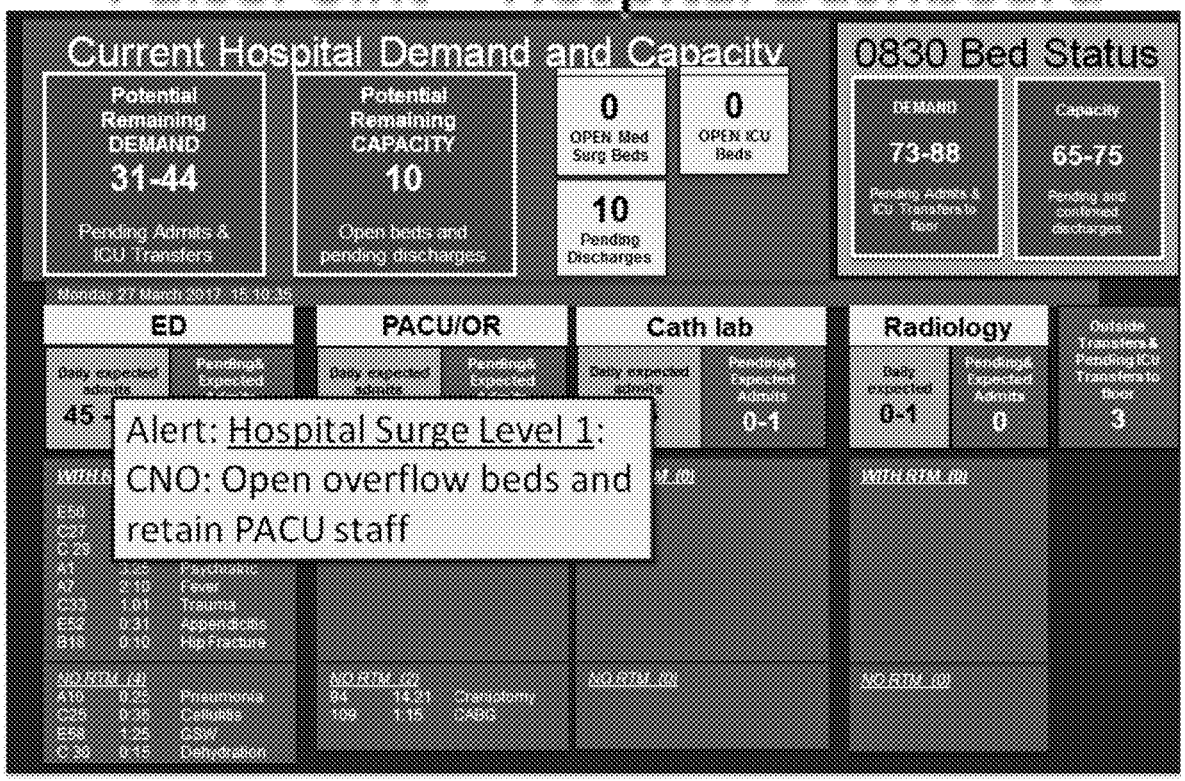
FIG. 24 illustrates one example alert generated from the example scenario illustrated in FIG. 23.
Figure 25:
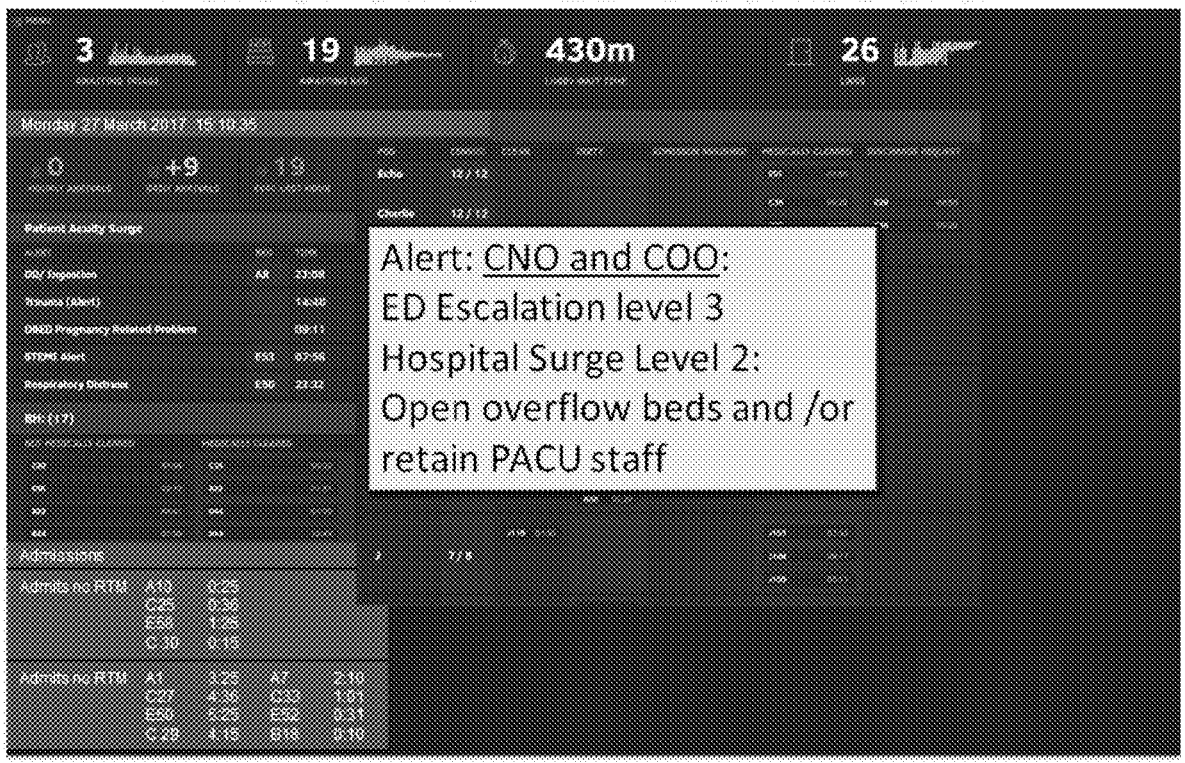
FIG. 25 illustrates another example dashboard screen illustrating an emergency department scenario and associated alerts generated.

FIG. 24 illustrates one example alert generated from the example scenario illustrated in FIG. 23. FIG. 25 illustrates another example dashboard screen illustrating an emergency department scenario and associated alerts generated. The present invention assesses variables such as patient arrival demand and capacity, arrival volume and hospital demand capacity by time of day to prescribe actions by staff and management. FIG. 26 illustrates a table illustrating example alerts generated by the system of the present invention when taking into consideration the ED and hospital admissions dashboards. For example, as illustrated, hospital surge alerts are generated when bed demand is greater than bed capacity (e.g., level 1 alert if bed demand is 20 over bed capacity, level 2 alert if bed demand is 30 over bed capacity, and level 3 alert if bed demand is 40 over capacity). These bed demand vs. capacity levels can also be combined as shown with emergency department escalation levels (e.g., 1, 2 or 3) to send predetermined alerts to predetermined hospital staff as set forth in FIG. 26. These alerts provide prescriptive action to hospital staff to take corrective procedures.

While certain embodiments of the present invention are described in detail above, the scope of the invention is not to be considered limited by such disclosure, and modifications are possible without departing from the spirit of the invention as evidenced by the following claims:

What is claimed is:

1. A method for tracking and facilitating the identification of bottlenecks and problem areas in hospital emergency departments, the method comprising:
    displaying in a first screen of a graphical user interface a first region comprised of a first indicator representing the number of patients waiting in the emergency department lobby;
    displaying in the first screen, a bed status region;
    displaying in the bed status region a listing of a plurality of areas of an emergency department, a listing of clean beds for each of the of the plurality of areas and a duration of time each of the clean beds have been in a clean bed status, a listing of dirty beds for each of the of the plurality of areas and a duration of time each of the dirty beds have been in a dirty bed status;
    displaying in the first screen a bed opportunities region aligned with the bed status region;
    displaying beds, by bed identifiers, that have patients with admissions assigned for each area of the emergency department;
    displaying, for each respective bed identifier, the duration of time each bed has been in the admissions assigned status;
    tracking, by a processor, the number of patients arriving in the emergency department for a plurality of predetermined periods of time;
    comparing, by the processor, the number of patients arriving in the emergency department for the plurality of predetermined periods of time to a historic patient arrival average taken over corresponding historical periods of time;
    displaying in the first screen an arrival surge region a number representing the number of patients arriving in the emergency department for a predetermined hourly time period over or under a historic patient arrival average for the predetermined hourly time period;
    displaying in the arrival surge region a number representing the number of patients arriving in the emergency department for a predetermined daily time period over or under a historic patient arrival average for the predetermined daily time period;
    incrementing or decrementing, by the processor, the number of patients arriving in the emergency department for the predetermined hourly time period and predetermined daily time period as more patients arrive at the emergency department or leave the emergency department; and
    wherein the first screen of the graphical user interface provides a unified view of the hourly and daily arrival surge information with the information relating to the status of each bed aligned with information relating to beds with admissions assigned and the duration the bed has been in the admissions assigned state for assisting in the identification of potential bottlenecks in admissions flow.

2. The method of claim 1, further comprising the step of displaying in the bed status region bed census data for each of the plurality of areas and wherein the bed census data is an indication of the number of occupied beds and total beds.

3. The method of claim 1, wherein the first indicator is a number representing the number of patients awaiting triage.

4. The method of claim 1, wherein the first indicator is a number representing the number of patients awaiting a bed in the emergency department.

5. The method of claim 1, wherein the first indicator is a number representing the number of patients awaiting triage plus the number of patients awaiting a bed in the emergency department.

6. The method of claim 1, wherein the first indicator is a number representing the number of patients awaiting triage, and wherein the method is further comprised of the step of displaying in the first region a second indicator representing the number of patients awaiting a bed in the emergency department.

7. The method of claim 1, further comprising the steps of:
    tracking, by a processor, current hospital surge by comparing current hospital bed demand over bed capacity;
    sending a first alert to predetermined hospital staff to take a first action for reducing bottlenecks in the hospital when the current hospital surge is at or over a first predetermined threshold level; and
    sending a second alert to predetermined hospital staff to take a second action for reducing bottlenecks in the hospital when the current hospital surge is at or over a second predetermined threshold level.

8. The method of claim 1, wherein one of the predetermined periods of time is the current hour and the corresponding historical periods of time are the same hour as the current hour from the previous 1, 2, 51 and 52 weeks.

9. The method of claim 1, wherein one of the predetermined periods of time is the current day and the corresponding historical periods of time are the same day as the current day from the previous 1, 2, 51 and 51 weeks.

10. The method of claim 1, further comprising the step of:
    displaying in the arrival surge region the number of patients who arrived by an emergency vehicle within the last hour.

11. The method of claim 1, further comprising the step of:
    displaying in the first region a number representing the number of patients who left the emergency department without being seen for a predetermined time period.

12. The method of claim 1, further comprising the steps of:
    displaying in the first screen an acuity surge region;
    displaying in the acuity surge region a listing of patients in the emergency department with serious conditions;
    displaying the arrival time for each of the patients listed with serious conditions.

13. The method of claim 1 wherein aligned means that each area of the emergency department is displayed in a separate row in the graphical user interface.

14. The method of claim 1, further comprising the steps of:
    displaying beds, by bed identifiers, that have medically cleared patients for each area of the emergency department;
    displaying, for each respective bed identifier, the duration of time each bed has been in the medically cleared status.

15. The method of claim 14, further comprising the steps of:
displaying beds, by bed identifiers, that have patients with discharge requests for each area of the emergency department;
displaying, for each respective bed identifier, the duration of time each bed has been in the discharge requested status.

16. The method of claim 1, further comprising the steps of:
displaying in the first screen a behavioral health region;
displaying in the behavioral health region a listing of beds in the emergency department that have medically cleared patients;
displaying for each respective medically cleared patient, the duration of time each patient has been in the medically cleared status.

17. The method of claim 16, further comprising the step of:
sending a first alert to a first predetermined staff member if a first patient stays in the medically cleared status for more than a first predetermined duration of time.

18. The method of claim 16, further comprising the step of:
sending a second alert to a second predetermined staff member if the first patient stays in the medically cleared status for more than a second predetermined duration of time.

19. The method of claim 1, further comprising the steps of:
sending a first alert to a first predetermined staff member if more than a first predetermined number of patients are waiting in the lobby of the emergency department;
sending a second alert to a second predetermined staff member if more than a second predetermined number of patients are waiting in the lobby of the emergency department.

20. The method of claim 1, further comprising the steps of:
sending a first alert to a first predetermined staff member if more than a first predetermined number of patients have left the emergency department without being seen or triaged;
sending a second alert to a second predetermined staff member if more than a second predetermined number of patients have left the emergency department without being seen or triaged.

21. The method of claim 1, further comprising the steps of:
sending a first alert to a first predetermined staff member if a longest lobby wait time of the emergency department is over a first predetermined length of time;
sending a second alert to a second predetermined staff member if a longest lobby wait time of the emergency department is over a second predetermined length of time.

22. The method of claim 1, further comprising the steps of:
sending a first alert to a first predetermined staff member if a patient has been in an admitted status over a first predetermined length of time;
sending a second alert to a second predetermined staff member if a patient has been in an admitted status over a second predetermined length of time.

23. The method of claim 1, further comprising the steps of:
sending a first alert to a first predetermined staff member if a patient has been in a ready-to-move status over a first predetermined length of time;
sending a second alert to a second predetermined staff member if a patient has been in a ready-to-move status over a second predetermined length of time.

24. The method of claim 1, further comprising the steps of:
sending a first alert to a first predetermined staff member if a patient has been in an inpatient-bed-assigned status over a first predetermined length of time;
sending a second alert to a second predetermined staff member if a patient has been in an inpatient-bed-assigned status over a second predetermined length of time.

25. A method for tracking and facilitating the identification of bottlenecks and problem areas in hospitals and emergency departments, the method comprising:
displaying in a first screen of a graphical user interface a first region comprised of a first indicator representing the number of patients waiting in the emergency department lobby;
displaying in the first screen a bed opportunities region aligned with the bed status region;
displaying beds, by bed identifiers, that have patients with admissions assigned for each area of the emergency department;
displaying, for each respective bed identifier, the duration of time each bed has been in the admissions assigned status;
tracking, by a processor, the number of patients arriving in the emergency department for a plurality of predetermined periods of time;
comparing, by the processor, the number of patients arriving in the emergency department for the plurality of predetermined periods of time to a historic patient arrival average taken over corresponding historical periods of time;
displaying in the first screen an arrival surge region a number representing the number of patients arriving in the emergency department for a predetermined hourly time period over or under a historic patient arrival average for the predetermined hourly time period;
displaying in the arrival surge region a number representing the number of patients arriving in the emergency department for a predetermined daily time period over or under a historic patient arrival average for the predetermined daily time period;
incrementing or decrementing, by the processor, the number of patients arriving in the emergency department for the predetermined hourly time period and predetermined daily time period as more patients arrive at the emergency department or leave the emergency department; and
wherein the first screen of the graphical user interface provides a unified view of the hourly and daily arrival surge information with the information relating to the status of each bed aligned with information relating to beds with admissions assigned and the duration the bed has been in the admissions assigned state for assisting in the identification of potential bottlenecks in admissions flow.

26. The method of claim 25, further comprising the steps of:
displaying in the first screen, a bed status region;
displaying in the bed status region a listing of a plurality of areas of an emergency department, bed census data for each of the plurality of areas, a listing of clean beds for each of the of the plurality of areas and a duration of time each of the clean beds have been in a clean bed status, a listing of dirty beds for each of the of the plurality of areas and a duration of time each of the dirty beds have been in a dirty bed status;

wherein the bed census is an indication of the number of occupied beds and total beds.

27. The method of claim 25, wherein the first indicator is a number representing the number of patients awaiting triage.

28. The method of claim 25, wherein the first indicator is a number representing the number of patients awaiting a bed in the emergency department.

29. The method of claim 25, wherein the first indicator is a number representing the number of patients awaiting triage plus the number of patients awaiting a bed in the emergency department.

30. The method of claim 25, wherein the first indicator is a number representing the number of patients awaiting triage, and wherein the method is further comprised of the step of displaying in the first region a second indicator representing the number of patients awaiting a bed in the emergency department.

31. The method of claim 25, wherein one of the predetermined periods of time is the current hour and the corresponding historical periods of time are the same hour as the current hour from the previous 1, 2, 51 and 52 weeks.

32. The method of claim 25, wherein one of the predetermined periods of time is the current day and the corresponding historical periods of time are the same day as the current day from the previous 1, 2, 51 and 52 weeks.

33. The method of claim 25, further comprising the steps of:
tracking, by a processor, current hospital surge by comparing current hospital bed demand over bed capacity;
sending a first alert to predetermined hospital staff to take a first action for reducing bottlenecks in the hospital when the current hospital surge is at or over a first predetermined threshold level; and
sending a second alert to predetermined hospital staff to take a second action for reducing bottlenecks in the hospital when the current hospital surge is at or over a second predetermined threshold level.

34. The method of claim 25, further comprising the step of:
displaying in the arrival surge region the number of patients who arrived by an emergency vehicle within the last hour.

35. The method of claim 25, further comprising the step of:
displaying in the first region a number representing the number of patients who left the emergency department without being seen for a predetermined time period.

36. The method of claim 25, further comprising the steps of:
displaying in the first screen an acuity surge region;
displaying in the acuity surge region a listing of patients in the emergency department with serious conditions;
displaying the arrival time for each of the patients listed with serious conditions.

37. The method of claim 25 wherein aligned means that each area of the emergency department is displayed in a separate row in the graphical user interface.

38. The method of claim 25, further comprising the steps of:
displaying beds, by bed identifiers, that have medically cleared patients for each area of the emergency department;
displaying, for each respective bed identifier, the duration of time each bed has been in the medically cleared status.

39. The method of claim 38, further comprising the step of:
displaying beds, by bed identifiers, that have patients with discharge requests for each area of the emergency department;
displaying, for each respective bed identifier, the duration of time each bed has been in the discharge requested status.

40. The method of claim 25, further comprising the steps of:
displaying in the first screen a behavioral health region;
displaying in the behavioral health region a listing of beds in the emergency department that have medically cleared patients;
displaying for each respective medically cleared patient, the duration of time each patient has been in the medically cleared status.

41. The method of claim 40, further comprising the step of:
sending a first alert to a first predetermined staff member if a first patient stays in the medically cleared status for more than a first predetermined duration of time.

42. The method of claim 41, further comprising the step of:
sending a second alert to a second predetermined staff member if the first patient stays in the medically cleared status for more than a second predetermined duration of time.

43. The method of claim 25, further comprising the steps of:
sending a first alert to a first predetermined staff member if more than a first predetermined number of patients are waiting in the lobby of the emergency department;
sending a second alert to a second predetermined staff member if more than a second predetermined number of patients are waiting in the lobby of the emergency department.

44. The method of claim 25, further comprising the steps of:
sending a first alert to a first predetermined staff member if more than a first predetermined number of patients have left the emergency department without being seen or triaged;
sending a second alert to a second predetermined staff member if more than a second predetermined number of patients have left the emergency department without being seen or triaged.

45. The method of claim 25, further comprising the steps of:
sending a first alert to a first predetermined staff member if a longest lobby wait time of the emergency department is over a first predetermined length of time;
sending a second alert to a second predetermined staff member if the longest lobby wait time of the emergency department is over a second predetermined length of time.

46. The method of claim 25, further comprising the steps of:
sending a first alert to a first predetermined staff member if a patient has been in an admitted status over a first predetermined length of time;

sending a second alert to a second predetermined staff member if a patient has been in an admitted status over a second predetermined length of time.

47. The method of claim 25, further comprising the steps of:
sending a first alert to a first predetermined staff member if a patient has been in a ready-to-move status over a first predetermined length of time;
sending a second alert to a second predetermined staff member if a patient has been in a ready-to-move status over a second predetermined length of time.

48. The method of claim 25, further comprising the steps of:
sending a first alert to a first predetermined staff member if a patient has been in an inpatient-bed-assigned status over a first predetermined length of time;
sending a second alert to a second predetermined staff member if a patient has been in an inpatient-bed-assigned status over a second predetermined length of time.

49. A system for tracking emergency room patients, resources and queues and for providing a unified graphical interface structure for facilitating process flow improvements and resource management, the system comprising:
a graphical user interface adapted to display in a first screen;
a processing system, the processing system programmed with instructions for executing on the processing system for: 1) displaying in the first screen a first region comprised of a first indicator representing the number of patients waiting in the emergency department lobby; 2) displaying in the first screen, a bed status region; 3) displaying in the bed status region a listing of a plurality of areas of an emergency department, a listing of clean beds for each of the plurality of areas and a duration of time each of the clean beds have been in a clean bed status, a listing of dirty beds for each of the plurality of areas and a duration of time each of the dirty beds have been in a dirty bed status;
wherein the processing system is programmed with instructions for executing on the processing system for 4) displaying in the first screen a bed opportunities region aligned with the bed status region; 5) displaying beds, by bed identifiers, that have patients with admissions assigned for each area of the emergency department; 6) displaying, for each respective bed identifier, the duration of time each bed has been in the admissions assigned status; 7) tracking the number of patients arriving in the emergency department for a plurality of predetermined periods of time; 8) comparing the number of patients arriving in the emergency department for the plurality of predetermined periods of time to a historic patient arrival average taken over corresponding historical periods of time; 9) displaying in the first screen an arrival surge region a number representing the number of patients arriving in the emergency department for a predetermined hourly time period over or under a historic patient arrival average for the predetermined hourly time period; 10) displaying in the arrival surge region a number representing the number of patients arriving in the emergency department for a predetermined daily time period over or under a historic patient arrival average for the predetermined daily time period; and 11) incrementing or decrementing the number of patients arriving in the emergency department for the predetermined hourly time period and predetermined daily time period as more patients arrive at the emergency department or leave the emergency department; and
wherein the first screen of the graphical user interface provides a unified view of the hourly and daily arrival surge information with the information relating to the status of each bed aligned with information relating to beds with admissions assigned and the duration the bed has been in the admissions assigned state for assisting in the identification of potential bottlenecks in admissions flow.

50. The system of claim 49, further comprising the step of displaying in the bed status region bed census data for each of the plurality of areas and wherein the bed census data is an indication of the number of occupied beds and total beds.

51. The system of claim 49, wherein the first indicator is a number representing the number of patients awaiting triage.

52. The system of claim 49, wherein the first indicator is a number representing the number of patients awaiting a bed in the emergency department.

53. The system of claim 49, wherein the first indicator is a number representing the number of patients awaiting triage plus the number of patients awaiting a bed in the emergency department.

54. The system of claim 49, wherein the first indicator is a number representing the number of patients awaiting triage, and wherein the processing system is programmed with instructions for executing on the processing system for displaying in the first region a second indicator representing the number of patients awaiting a bed in the emergency department.

55. The system of claim 49, wherein the processing system is programmed with instructions for executing on the processing system for:
tracking, by a processor, current hospital surge by comparing current hospital bed demand over bed capacity;
sending a first alert to predetermined hospital staff to take a first action for reducing bottlenecks in the hospital when the current hospital surge is at or over a first predetermined threshold level; and
sending a second alert to predetermined hospital staff to take a second action for reducing bottlenecks in the hospital when the current hospital surge is at or over a second predetermined threshold level.

56. The system of claim 49, wherein one of the predetermined periods of time is the current hour and the corresponding historical periods of time are a same hour as the current hour from the previous 1, 2, 51 and 52 weeks.

57. The system of claim 49, wherein one of the predetermined periods of time is the current day and the corresponding historical periods of time are a same day as the current day from the previous 1, 2, 51 and 52 weeks.

58. The system of claim 49, wherein the processing system is programmed with instructions for executing on the processing system for displaying in the arrival surge region the number of patients who arrived by an emergency vehicle within the last hour.

59. The system of claim 49, wherein the processing system is programmed with instructions for executing on the processing system for displaying in the first region a number representing the number of patients who left the emergency department without being seen for a predetermined time period.

60. The system of claim 49, wherein the processing system is programmed with instructions for executing on the processing system for 4) displaying in the first screen an acuity surge region; 5) displaying in the acuity surge region a listing of patients in the emergency department with serious conditions; and 6) displaying the arrival time for each of the patients listed with serious conditions.

61. The system of claim 49 wherein aligned means that each area of the emergency department is displayed in a separate row in the graphical user interface.

62. The system of claim 49, wherein the processing system is programmed with instructions for executing on the processing system for 7) displaying beds, by bed identifiers, that have medically cleared patients for each area of the emergency department; and 8) displaying, for each respective bed identifier, the duration of time each bed has been in the medically cleared status.

63. The method of claim 62, wherein the processing system is programmed with instructions for executing on the processing system for 9) displaying beds, by bed identifiers, that have patients with discharge requests for each area of the emergency department; and 10) displaying, for each respective bed identifier, the duration of time each bed has been in the discharge requested status.

64. The system of claim 49, wherein the processing system is programmed with instructions for executing on the processing system for 4) displaying in the first screen a behavioral health region; 5) displaying in the behavioral health region a listing of beds in the emergency department that have medically cleared patients; 6) displaying for each respective medically cleared patient, the duration of time each patient has been in the medically cleared status.

65. The system of claim 49, wherein the processing system is programmed with instructions for executing on the processing system for: 4) sending a first alert to a first predetermined staff member if a first patient stays in the medically cleared status for more than a first predetermined duration of time; and 5) sending a second alert to a second predetermined staff member if the first patient stays in the medically cleared status for more than a second predetermined duration of time.

66. The system of claim 49, wherein the processing system is programmed with instructions for executing on the processing system for 4) sending a first alert to a first predetermined staff member if more than a first predetermined number of patients are waiting in the lobby of the emergency department; 5) sending a second alert to a second predetermined staff member if more than a second predetermined number of patients are waiting in the lobby of the emergency department.

67. The system of claim 49, wherein the processing system is programmed with instructions for executing on the processing system for 4) sending a first alert to a first predetermined staff member if more than a first predetermined number of patients have left the emergency department without being seen or triaged; and 5) sending a second alert to a second predetermined staff member if more than a second predetermined number of patients have left the emergency department without being seen or triaged.

68. The system of claim 49, wherein the processing system is programmed with instructions for executing on the processing system for 4) sending a first alert to a first predetermined staff member if a longest lobby wait time of the emergency department is over a first predetermined length of time; and 5) sending a second alert to a second predetermined staff member if a longest lobby wait time of the emergency department is over a second predetermined length of time.

69. The system of claim 49, wherein the processing system is programmed with instructions for executing on the processing system for: storing the number of patients waiting for admission into the hospital; storing the number of patients predicted to be discharged; and sending a first alert to a predetermined staff member if the first indicator representing the number of patients waiting in the emergency department lobby is larger than a predetermined number and if the number of patients awaiting for admissions into the hospital is larger than the number of patients predicted to be discharged.

70. The system of claim 50, wherein the processing system is programmed with instructions for executing on the processing system for alerting the predetermined staff member to open additional overflow beds and call in additional staff members if the hospital is understaffed.

71. The system of claim 69, wherein the first indicator represents the number of patients waiting for a bed in the emergency room.

72. The system of claim 49, wherein the processing system is programmed with instructions for executing on the processing system for: storing the number of patients waiting in the emergency department for a medical test; storing the number of available resources for conducting the medical test; and sending a first alert to a predetermined staff member if the first indicator representing the number of patients waiting in the emergency department lobby is larger than a predetermined number and if the number of available resources for conducting the medical test is not sufficient to handle the number of patients waiting for the medical test.

73. The system of claim 72, wherein the first indicator represents the number of patients waiting for a bed in the emergency department and wherein the first alert recommends increasing resources for conducting the medical test.

* * * * *

UNITED STATES PATENT AND TRADEMARK OFFICE
CERTIFICATE OF CORRECTION

PATENT NO. : 10,839,959 B2
APPLICATION NO. : 15/581228
DATED : November 17, 2020
INVENTOR(S) : Dreyer Page 1 of 1

It is certified that error appears in the above-identified patent and that said Letters Patent is hereby corrected as shown below:

In the Claims

In Claim 9, Column 34, Line 41 - please delete "51 weeks" and please add --52 weeks--.

Signed and Sealed this
Twenty-ninth Day of December, 2020

Andrei Iancu
*Director of the United States Patent and Trademark Office*